US008660312B2

(12) United States Patent
Cui et al.

(10) Patent No.: US 8,660,312 B2
(45) Date of Patent: Feb. 25, 2014

(54) QUANTITATIVE DIFFERENTIAL INTERFERENCE CONTRAST (DIC) DEVICES FOR COMPUTED DEPTH SECTIONING

(75) Inventors: Xiquan Cui, Pasadena, CA (US); Changhuei Yang, Pasadena, CA (US)

(73) Assignee: California Institute of Technology, Pasadena, CA (US)

(*) Notice: Subject to any disclaimer, the term of this patent is extended or adjusted under 35 U.S.C. 154(b) by 537 days.

(21) Appl. No.: 12/690,952

(22) Filed: Jan. 21, 2010

(65) Prior Publication Data

US 2010/0195873 A1     Aug. 5, 2010

Related U.S. Application Data

(60) Provisional application No. 61/205,487, filed on Jan. 21, 2009.

(51) Int. Cl.
*G06K 9/00*          (2006.01)

(52) U.S. Cl.
USPC .......................................................... 382/106

(58) Field of Classification Search
USPC .................. 33/719; 250/201.9; 348/E13.017, 348/E13.057; 356/494, 499; 382/106; 702/166
See application file for complete search history.

(56) References Cited

U.S. PATENT DOCUMENTS

| | | | |
|---|---|---|---|
| 4,438,330 A | 3/1984 | Hardy | |
| 4,692,027 A | 9/1987 | MacGovern et al. | |
| 4,737,621 A | 4/1988 | Gonsiorowski et al. | |
| 4,980,716 A | 12/1990 | Suzuki et al. | |
| 4,981,362 A | 1/1991 | DeJong et al. | |
| 5,124,927 A * | 6/1992 | Hopewell et al. | 700/121 |
| 5,196,350 A | 3/1993 | Backman et al. | |
| 5,233,174 A | 8/1993 | Zmek | |

(Continued)

FOREIGN PATENT DOCUMENTS

| | | |
|---|---|---|
| EP | 1 371 965 | 12/2003 |
| EP | 1 635 692 | 3/2006 |

(Continued)

OTHER PUBLICATIONS

Lew et al., ("Interference of a four-hole aperture for on-chip quantitative two-dimensional differential phase imaging"), Optic Letters vol. 32, No. 20, pp. 2963-2965, Oct. 15, 2007.*

(Continued)

*Primary Examiner* — Gregory F Cunningham
(74) *Attorney, Agent, or Firm* — Sheila Martinez-Lemke; Weaver Austin Villeneuve & Sampson LLP

(57) ABSTRACT

Embodiments of the present invention relate to a method for computing depth sectioning of an object using a quantitative differential interference contrast device having a wavefront sensor with one or more structured apertures, a light detector and a transparent layer between the structured apertures and the light detector. The method comprises receiving light, by the light detector, through the one or more structured apertures. The method also measures the amplitude of an image wavefront, and measures the phase gradient in two orthogonal directions of the image wavefront based on the light. The method can then reconstruct the image wavefront using the amplitude and phase gradient. The method can then propagate the reconstructed wavefront to a first plane intersecting an object at a first depth. In one embodiment, the method propagates the reconstructed wavefront to additional planes and generates a three-dimensional image based on the propagated wavefronts.

25 Claims, 18 Drawing Sheets

(56) References Cited

U.S. PATENT DOCUMENTS

| | | | |
|---|---|---|---|
| 5,300,766 A * | 4/1994 | Granger et al. | 250/201.9 |
| 5,362,653 A | 11/1994 | Carr et al. | |
| 5,426,505 A | 6/1995 | Geiser et al. | |
| 5,795,755 A | 8/1998 | Lemelson | |
| 5,798,262 A | 8/1998 | Garini et al. | |
| 5,973,316 A | 10/1999 | Ebbesen et al. | |
| 6,130,419 A * | 10/2000 | Neal | 250/201.9 |
| 6,143,247 A | 11/2000 | Sheppard, Jr. et al. | |
| 6,499,499 B2 | 12/2002 | Dantsker et al. | |
| 6,753,131 B1 | 6/2004 | Rogers et al. | |
| 6,858,436 B2 | 2/2005 | Zenhausern et al. | |
| 6,987,255 B2 | 1/2006 | Smith | |
| 7,045,781 B2 | 5/2006 | Adamec et al. | |
| 7,113,268 B2 | 9/2006 | Gerwe et al. | |
| 7,250,598 B2 | 7/2007 | Hollingsworth et al. | |
| 7,271,885 B2 | 9/2007 | Schermer | |
| 7,283,229 B2 | 10/2007 | Noguchi et al. | |
| 7,399,445 B2 | 7/2008 | Kuroda et al. | |
| 7,641,856 B2 | 1/2010 | Padmanabhan et al. | |
| 7,671,987 B2 | 3/2010 | Padmanabhan et al. | |
| 7,738,695 B2 | 6/2010 | Shorte et al. | |
| 7,751,048 B2 | 7/2010 | Yang et al. | |
| 7,768,654 B2 | 8/2010 | Cui et al. | |
| 7,773,227 B2 | 8/2010 | Yang et al. | |
| 7,864,333 B1 | 1/2011 | Olczak et al. | |
| 7,982,883 B2 | 7/2011 | Cui et al. | |
| 8,039,776 B2 | 10/2011 | Cui et al. | |
| 8,120,765 B2 | 2/2012 | Huang et al. | |
| 8,189,204 B2 | 5/2012 | Cui et al. | |
| 8,314,933 B2 | 11/2012 | Cui et al. | |
| 8,325,349 B2 | 12/2012 | Cui et al. | |
| 8,411,282 B2 | 4/2013 | Cui et al. | |
| 8,416,400 B2 | 4/2013 | Cui et al. | |
| 8,525,091 B2 | 9/2013 | Cui et al. | |
| 2003/0142291 A1 | 7/2003 | Padmanabhan et al. | |
| 2003/0174992 A1 | 9/2003 | Levene et al. | |
| 2003/0203502 A1 | 10/2003 | Zenhausern et al. | |
| 2004/0156610 A1 | 8/2004 | Charlton et al. | |
| 2004/0175734 A1 | 9/2004 | Stahler et al. | |
| 2004/0190116 A1 | 9/2004 | Lezec et al. | |
| 2004/0224380 A1 | 11/2004 | Chou et al. | |
| 2005/0007603 A1 * | 1/2005 | Arieli et al. | 356/601 |
| 2005/0088735 A1 * | 4/2005 | Olszak | 359/434 |
| 2005/0161594 A1 | 7/2005 | Hollingsworth et al. | |
| 2005/0271548 A1 | 12/2005 | Yang et al. | |
| 2006/0003145 A1 | 1/2006 | Hansen et al. | |
| 2006/0013031 A1 | 1/2006 | Ravkin et al. | |
| 2006/0175528 A1 | 8/2006 | Greenaway et al. | |
| 2007/0069999 A1 * | 3/2007 | Gu et al. | 345/84 |
| 2007/0172745 A1 | 7/2007 | Smith | |
| 2007/0207061 A1 | 9/2007 | Yang et al. | |
| 2007/0258096 A1 | 11/2007 | Cui et al. | |
| 2009/0079992 A1 * | 3/2009 | Doerband | 356/496 |
| 2009/0225319 A1 | 9/2009 | Lee et al. | |
| 2009/0276188 A1 | 11/2009 | Cui et al. | |
| 2010/0296094 A1 | 11/2010 | Yang et al. | |
| 2010/0309457 A1 | 12/2010 | Cui et al. | |
| 2011/0063623 A1 | 3/2011 | Cui et al. | |
| 2011/0075254 A1 | 3/2011 | Cui et al. | |
| 2011/0085219 A1 * | 4/2011 | Yang et al. | 359/15 |
| 2011/0170105 A1 | 7/2011 | Cui et al. | |
| 2011/0181884 A1 | 7/2011 | Cui et al. | |
| 2012/0026509 A1 | 2/2012 | Cui et al. | |
| 2012/0061554 A1 | 3/2012 | Cui et al. | |
| 2012/0211644 A1 | 8/2012 | Zheng et al. | |
| 2012/0250027 A1 | 10/2012 | Zheng et al. | |

FOREIGN PATENT DOCUMENTS

| | | |
|---|---|---|
| EP | 1 787 156 | 5/2007 |
| JP | 2003-207454 A | 7/2003 |
| JP | 2003-0524779 A | 8/2003 |
| JP | 2004-505272 A | 2/2004 |
| WO | WO 02/10713 A2 | 2/2002 |
| WO | WO 2004/038484 A2 | 5/2004 |
| WO | WO 2005/121749 | 12/2005 |
| WO | WO 2008/112416 | 9/2008 |
| WO | WO 2009/111573 | 9/2009 |
| WO | WO 2009/111577 | 9/2009 |
| WO | WO 2010/090849 | 8/2010 |
| WO | WO 2010/141702 | 12/2010 |

OTHER PUBLICATIONS

Lew, Matthew, et al., "Interference of a four-hole aperture for on-chip quantitative two-dimensional differential phase imaging," Optics Letters, vol. 32, No. 20, pp. 2963-2965 (Oct. 2007).*

Albensi, Benedict C., et al., "Elements of Scientific Visualization in Basic Neuroscience Research," BioScience, vol. 54, No. 12, pp. 1127-1137 (Dec. 2004).

Anand, Arun, et al., "Wavefront sensing with random amplitude mask and phase retrieval," Optics Letters, vol. 32, No. 11, pp. 1584-1585 (Jun. 2007).

Arninson, M. R., et al., "Linear Phase Imaging Using Differential Interference Contast Microscopy," Journal of Microscoy, vol. 214, Part I, pp. 7-12 (Apr. 2004).

Barty, A., et al., "Quantitative optical phase microscopy," Optics Letters, vol. 23, pp. 817-819 (1998).

Betzig, Eric, et al., "Imaging Intracellular Fluorescent Proteins at Nanometer Resolution," Science, vol. 313, pp. 1642-1645 (Sep. 2006).

Booth, Martin J., et al. , "Adaptive aberration correction in confocal microscope," Proceedings of the National Academy of Sciences of the United States of America, vol. 99, No. 9, pp. 5788-5792 (Apr. 2002).

Bouwkamp, C. J., "Diffraction theory," Reports on Progress in Physics XVIII, pp. 35-100 (1954).

Carmon, Yuval, and Ribak, Erez N., "Phase retrieval by demodulation of a Hartmann-Shack sensor," Opt. Commun., vol. 215, pp. 285-288 (2003).

Chalut, Kevin J., et al., "Quantitative phase microscopy with asynchronous digital holography," Optics Express, vol. 15, No. 6, pp. 3047-3052 (Mar. 2007).

Choi, Wonshik, et al., "Tomographic phase microscopy," Nature Methods, vol. 4, No. 9, pp. 717-719 (Sep. 2007).

Cogswell, C. J., et al., "Confocal differential contrast interference (DIC) microscopy: including a theoretical analysis of conventional and confocal DIC imaging," Journal of Microcscopy, vol. 165, Pt. 1, pp. 81-101 (Jan. 1992).

Creath, Katherine, "Phase-measurement interferometry techniques," Prog. Opt., vol. 26, pp. 349-393 (1988).

Cui, Xiquan, et al., "Portable optical microscope-on-a-chip," P{roc. of SPIE, vol. 6095, pp. 609509-1-609509-8 (Jan. 2006).

Cui, Xiquan, et al., "Quantitative differential interference contrast microscopy based on structured-aperture interference," Applied Physics Letters, vol. 93, pp. 091113-1-091113-3 (2008).

Cui, Xiquan, et al., "Slanted hole array beam profiler (SHArP)—A high-resolution portable beam profiler based on a linear aperture array," Optics Letters, vol. 31, No. 21, pp. 3161-3163 (Nov. 2006).

Davidson, Michael, et al., "Differential interference contrast, 'Comparison of wavelength of DIC microscopy'," Florida State University website, last website modification Jul. 26, 2005, printed Apr. 13, 2009, 12 pages.

Doyle, Patrick, et al., "Self-Assembled Magnetic Matrices for DNA Separation Chips," Science, vol. 295, No. 5563, p. 2237 (Mar. 2002).

Dunn, et al., "Introduction to Confocal Microscopy," available from MicroscopyU at http://www.microscopyu.com/articles/confocal (2007).

Ebbesen, T. W., et al., "Extraordinary optical transmission through sub-wavelength hole arrays," Nature, vol. 391 (6668), pp. 667-669 (Feb. 1998).

Fletcher, R., and Reeves, C. M., "Function minimization by conjugate gradients," Comput. J. 7, 149-154 (1964).

Fu, Anne Y., et al., "A microfabricated fluorescence-activated cell sorter," Nature Biotechnology, vol. 17, pp. 1109-1111 (Nov. 1999).

(56) References Cited

OTHER PUBLICATIONS

Garcia De Abajo, F. J., "Light transmission through a single cylindrical hole in a metallic film," Optics Express, vol. 10, No. 25, pp. 1475-1484 (2002).
Haglund, Michael M., et al., "Enhanced Optical Imaging of Human Gliomas and Tumor Margins," Neurosurgery, vol. 38, pp. 308-317 (Feb. 1996).
Heng, Xin, et al., "Optofluidic Microscope, a miniature microscope on a chip," 9th International Conference on Miniaturized Systems for Chemistry and Life Sciences (μTAS) (2005).
Heng, Xin, et al., "Optofluidic Microscopy—a method for implementing a high resolution optical microscope on a chip," Lab Chip, vol. 6, pp. 1274-1276 (2006).
Hoffman, Robert, and Gross, Leo, "Modulation Contrast Microscope," Applied Optics, vol. 14, No. 5, pp. 1169-1176 (May 1975).
Hogenboom, D. O., et al., "Three-dimensional images generated by quadrature interferometry," Optics Letters, vol. 23, No. 10, pp. 783-785 (May 1998).
Ikeda, Takahiro, et al., "Hilbert phase microscopy for investigating fast dynamics in transparent systems," Optics Letters, vol. 30, No. 10, pp. 1165-1167 (May 2005).
Kagalwala, Farhana, and Kanade, Takeo, "Reconstructing Specimens Using DIC Microscope Images," IEEE Transactions on Systems, Man, and Cybernetics-Part B: Cybernetics, vol. 33, No. 5 pp. 307-315 (Oct. 2003).
Lezec, Henri J., et al., "Beaming Light from a Subwavelength Aperture," Science, vol. 297, No. 5582, pp. 820-822 (Aug. 2002).
Lezec, Henri J., and Thio, Tineke, "Diffracted evanescent wave model for enhanced and suppressed optical transmission through subwavelength hole arrays," Optics Express, vol. 12, No. 16, pp. 3629-3651 (Aug. 2004).
Liang, Junzhong Z., et al., "Supernormal vision and high-resolution retinal imaging through adaptive optics," Journal of the Optical Society of America, vol. 14, No. 11, pp. 2884-2892 (Nov. 1997).
Liu, Shaorong, "A microfabricated hybrid device for DNA sequencing," Electrophoresis 2003, vol. 24(21), pp. 3755-3761 (2003).
Marquet, Pierre, et al., "Digital holographic microscopy: a noninvasive contrast imaging technique allowing quantitative visualization of living cells with subwavelength axial accuracy," Optics Letters, vol. 30, No. 5, pp. 468-470 (Mar. 2005).
Mehta, Shalin B., and Sheppard, Colin J. R., "Quantitative phase-gradient imaging at high resolution with asymmetric illumination-based differential phase contrast," Optics Letters, vol. 34, No. 13, pp. 1924-1926 (Jul. 2009).
Murphy, et al., "Differential Interference Contrast (DIC)," available from Nikon MicrocopyU at http://www.microscopyu.com/articles/dic/dicindex.html (2007).
Popescu, Gabriel, et al., "Diffraction phase microscopy for quantifying cell structure and dynamics," Optics Letters, vol. 31, No. 6, pp. 775-777 (Mar. 2006).
Popescu, Gabriel, et al., "Optical Measurement of Cell Membrane Tension," Physical Review Letters 97, pp. 218101-1-218101-4 (Nov. 2006).
Preza, Chrysanthe, "Rotational-Diversity Phase Estimation from Differential-Interference Contrast Microscopy Images," J. Opt. Soc. Am. A, vol. 17, No. 3 (Mar. 2000).
Rappaz, Benjamin, et al., "Measurement of the integral refractive index and dynamic cell morphometry of living cells with digital holographic microscopy," Optics Express, vol. 13, pp. 9361-9373 (Nov. 2005).
Rueckel, Markus, et al., "Adaptive wavefront correction in two-photon microscopy using coherence-gated wavefront sensing," Proceedings of the National Academy of Sciences of the USA, vol. 103, No. 46, pp. 17137-17142 (Nov. 2006).
Rust, Michael J., et al., "Sub-diffraction-limit imaging by stochastic optical reconstruction microscopy (STORM)," Nature Methods, vol. 3, No. 10, pp. 793-795 (Oct. 2006).
Sarunic, Marinko V., et al., "Full-field swept-source phase microscopy," Optics Letters, vol. 31, No. 10, pp. 1462-1464 (May 2006).
Schwiegerling, Jim, and Neal, Daniel, "Historical Development of the Shack-Hartmann Wavefront Sensor," in Robert Shannon and Roland Shack: Legends in Applied Optics, edited by J. E. Harvey and R. B. Hooker_SPIE, Bellingham, WA, pp. 132-139 (2005).
Sommer, Ralf J., and Sternberg, Paul W., "Changes of Induction and Competence During the Evolution of Vulva Development in Nematodes," Science, vol. 265, pp. 114-118 (Jul. 1994).
Stanley, Samuel L. Jr, "Amoebiasis," The Lancet, vol. 361, pp. 1025-1034 (Mar. 2003).
Tegenfeldt, Jonas O., et al., "Micro- and nanofluidics for DNA analysis," Analytical and Bioanalytical Chemistry, 378(7), pp. 1678-1692 (Mar. 2004).
Tegenfeldt, Jonas O., et al., "Near-Field Scanner for Moving Molecules," Physical review letters, vol. 86, No. 7, pp. 1378-1381 (Feb. 2001).
Thompson, Russell E., et al., "Precise Nanometer Localization Analysis for Individual Fluorescent Probes," Biophysical Journal, vol. 82, No. 5, pp. 2775-2783 (May 2002).
Tokeshi, Manabu, et al., "Chemical processing on microchips for analysis, synthesis, and bioassay," Electrophoresis, vol. 24, No. 21, pp. 3583-3594 (2003).
Trau, Dieter, et al., "Genotyping on a complementary metal oxide semiconductor silicon polymerase chain reaction chip with integrated DNA microarray," Analytical Chemistry, vol. 74, No. 13, pp. 3168-3173 (2002).
Wu, Jigang, et al., "Full field phase imaging using a harmonically matched diffraction grating pair based homodyne quadrature interferometer," Applied Physics Letters, vol. 90, pp. 151123-1-151123-3 (Apr. 2007).
Yaqoob, Zahid, et al., "Harmonically-related diffraction gratings-based interferometer for quadrature phase measurements," Optics Express, vol. 14, No. 18, pp. 8127-8137 (2006).
Zernike, R., "Phase contrast, a new method for the microscopic observation of transparent objects," Physica IX, pp. 974-986 (Dec. 1942).
Wikipedia, "Adaptive optics," last modified Mar. 17, 2009.
Wikipedia, "Differential interference contrast microscopy," last modified Feb. 10, 2009.
Wikipedia, "Fresnel number," last modified on May 2, 2010.
Wikipedia, "Shack-Hartmann," last modified on Mar. 30, 2009.
Wikipedia, "Zone plate," last modified Apr. 2, 2009.
United States Patent and Trademark Office (USPTO) Office Action in U.S. Appl. No. 11/125,718 dated on Nov. 14, 2008.
United States Patent and Trademark Office (USPTO) Final Office Action in U.S. Appl. No. 11/125,718 dated on Jul. 1, 2009.
United States Patent and Trademark Office (USPTO) Notice of Allowance in U.S. Appl. No. 11/125,718 dated on Mar. 11, 2010.
United States Patent and Trademark Office (USPTO) Office Action in U.S. Appl. No. 12/797,132 dated on Oct. 15, 2010.
United States Patent and Trademark Office (USPTO) Office Action in U.S. Appl. No. 11/686,095 dated on Jan. 10, 2008.
United States Patent and Trademark Office (USPTO) Office Action in U.S. Appl. No. 11/686,095 dated on Jul. 17, 2008.
United States Patent and Trademark Office (USPTO) Office Action in U.S. Appl. No. 11/686,095 dated on Feb. 26, 2009.
United States Patent and Trademark Office (USPTO) Final Office Action in U.S. Appl. No. 11/686,095 dated on Oct. 28, 2009.
United States Patent and Trademark Office (USPTO) Notice of Allowance in U.S. Appl. No. 11/686,095 dated on Feb. 25, 2010.
United States Patent and Trademark Office (USPTO) Office Action in U.S. Appl. No. 12/785,635 dated on Oct. 15, 2010.
United States Patent and Trademark Office (USPTO) Office Action in U.S. Appl. No. 11/743,581 dated on May 22, 2009.
United States Patent and Trademark Office (USPTO) Final Office Action in U.S. Appl. No. 11/743,581 dated on Dec. 3, 2009.
United States Patent and Trademark Office (USPTO) Notice of Allowance in U.S. Appl. No. 11/743,581 dated on Mar. 26, 2010.
United States Patent and Trademark Office (USPTO) Notice of Allowance in U.S. Appl. No. 12/823,201 dated on Mar. 1, 2011.
United States Patent and Trademark Office (USPTO) Notice of Allowance in U.S. Appl. No. 12/823,201 dated on Mar. 11, 2011.
United States Patent and Trademark Office (USPTO) Office Action in U.S. Appl. No. 13/157,245 dated on Dec. 6, 2011.

(56) References Cited

OTHER PUBLICATIONS

United States Patent and Trademark Office (USPTO) Notice of Allowance in U.S. Appl. No. 13/157,245 dated on Aug. 23, 2012.
U.S. Allowed Claims for U.S. Appl. No. 13/157,245 dated on Dec. 3, 2012.
United States Patent and Trademark Office (USPTO) Notice of Allowance in U.S. Appl. No. 13/157,245 dated on Dec. 3, 2012.
United States Patent and Trademark Office (USPTO) Notice of Allowance in U.S. Appl. No. 12/792,059 dated on Dec. 14, 2011.
United States Patent and Trademark Office (USPTO) Restriction Requirement in U.S. Appl. No. 12/398,050 dated on Aug. 10, 2011.
United States Patent and Trademark Office (USPTO) Office Action in U.S. Appl. No. 12/398,050 dated on Nov. 14, 2011.
United States Patent and Trademark Office (USPTO) Notice of Allowance in U.S. Appl. No. 12/398,050 dated on Jul. 17, 2012.
United States Patent and Trademark Office (USPTO) Notice of Allowance in U.S. Appl. No. 12/398,050 dated on Aug. 28, 2012.
United States Patent and Trademark Office (USPTO) Office Action in U.S. Appl. No. 12/638,518 dated on Jan. 12, 2012.
United States Patent and Trademark Office (USPTO) Notice of Allowance in U.S. Appl. No. 12/638,518 dated on Feb. 14, 2012.
United States Patent and Trademark Office (USPTO) Notice of Allowance in U.S. Appl. No. 12/638,518 dated on Apr. 23, 2012.
United States Patent and Trademark Office (USPTO) Notice of Allowance in U.S. Appl. No. 12/638,518 dated on Aug. 24, 2012.
United States Patent and Trademark Office (USPTO) Office Action in U.S. Appl. No. 12/398,098 dated on May 25, 2011.
United States Patent and Trademark Office (USPTO) Final Office Action in U.S. Appl. No. 12/398,098 dated on Nov. 23, 2012.
United States Patent and Trademark Office (USPTO) Office Action in U.S. Appl. No. 12/435,165 dated on Apr. 12, 2011.
United States Patent and Trademark Office (USPTO) Notice of Allowance in U.S. Appl. No. 12/435,165 dated on Jun. 10, 2011.
United States Patent and Trademark Office (USPTO) Notice to File Corrected Application Papers in U.S. Appl. No. 12/435,165 dated on Jul. 25, 2011.
United States Patent and Trademark Office (USPTO) Office Action in U.S. Appl. No. 13/229,741 dated on Apr. 12, 2012.
United States Patent and Trademark Office (USPTO) U.S. Allowed Claims in U.S. Appl. No. 13/229,741 dated on Dec. 7, 2012.
United States Patent and Trademark Office (USPTO) Notice of Allowance in U.S. Appl. No. 13/229,741 dated on Dec. 7, 2012.
United States Patent and Trademark Office (USPTO) Office Action in U.S. Appl. No. 12/792,177 dated on Dec. 23, 2011.
United States Patent and Trademark Office (USPTO) Notice of Allowance in U.S. Appl. No. 12/792,177 dated on Aug. 29, 2012.
United States Patent and Trademark Office (USPTO) U.S. Allowed Claims in U.S. Appl. No. 12/792,177 dated on Dec. 10, 2012.
United States Patent and Trademark Office (USPTO) Notice of Allowance in U.S. Appl. No. 12/792,177 dated on Dec. 10, 2012.
United States Patent and Trademark Office (USPTO) Miscellaneous Action in U.S. Appl. No. 12/792,177 dated on Jan. 11, 2013.
PCT International Search Report dated Oct. 16, 2006 issued in PCT/US2005/016876.
PCT Written Opinion dated Oct. 16, 2006 issued in PCT/US2005/016876.
PCT International Preliminary Report on Patentability dated Dec. 4, 2006 issued in PCT/US2005/016876.
European Patent Office (EPO) European Supplementary Search Report dated Jan. 26, 2012 issued in EP Application No. 05 74 9488.2.
European Patent Office (EPO) Office Action dated Jun. 27, 2012 issued in EP Patent Application No. 05 749 488.2.
Japanese Patent Office (JPO) Office Action dated Jul. 26, 2011 issued in JPO patent Application No. 2007-515164.
Japanese Patent Office (JPO) Office Action dated May 8, 2012 issued in JPO patent Application No. 2007-515164.
PCT International Search Report dated Aug. 26, 2008 issued in PCT/US2008/054908.
PCT Written Opinion dated Aug. 26, 2008 issued in PCT/US2008/054908.
PCT International Preliminary Report on Patentability dated Sep. 15, 2009 issued in PCT/US2008/054908.
European Patent Office (EPO) European Supplementary Search Report dated Feb. 7, 2012 issued in EP Patent Application No. 08 730 664.3.
Japanese Patent Office (JPO) Office Action Jan. 24, 2012 issued in JPO patent Application No. 2009-553675.
PCT International Search Report dated Apr. 23, 2009 issued in PCT/US2009/036045.
PCT Written Opinion dated Apr. 23, 2009 issued in PCT/US2009/036045.
PCT International Preliminary Report on Patentability and Written Opinion dated Sep. 16, 2010 issued in PCT/US2009/036045.
European Search Report dated Feb. 11, 2013 issued in EP 09 716 850.4.
PCT International Search Report dated Jun. 29, 2009 issued in PCT/2009/036052.
PCT Written Opinion dated Jun. 29, 2009 issued in PCT/2009/036052.
PCT International Preliminary Report on Patentability and Written Opinion dated Sep. 16, 2010 issued in PCT/2009/036052.
PCT International Search Report and Written Opinion dated Jun. 29, 2010 issued in PCT/US2010/021561.
PCT International Preliminary Report on Patentability and Written Opinion dated Aug. 4, 2011 issued in PCT/US2010/021561.
European Patent Office (EPO) European Supplementary Search Report dated Jun. 11, 2012 issued in EP 10 738 939.7.
PCT International Search Report and Written Opinion dated Dec. 20, 2010 issued in PCT/US2010/037235.
PCT Preliminary Report on Patentability and Written Opinion dated Dec. 15, 2011 issued in PCT/US2010/037235.
Chinese First Office Action dated Nov. 1, 2012 issued in CN 201080024175.6.
"Surface Plasmon," Wikipedia, last modified Apr. 4, 2010.
Abramowitz et al., "Numerical Aperture and Resolution," Olympus Resource Center, downloaded from the Internet at: http://www.olympusmicro.com/primer/anatomy/numaperture.html on Aug. 13, 2012.
Adams, Mark L., et al., "Microfluidic Integration on detector arrays for absorption and fluorescence micro-spectrometers," *Sensors and Actuators A*, vol. 104, pp. 25-31 (2003).
Aigouy, L., et al., "Near-field analysis of surface waves launched at nanoslit apertures," Physical Review Letters, vol. 98, p. 153902 (2007).
Allen et al., "The Zeiss-Nomarski differential interference equipment for transmitted light microscopy," Z. wiss. Mikr 69, 89 (1969).
Aroian et al., "Multiple functions of let-23, a *Caenorhabditis elegans* recetor tyrosine kinase gene required for vulval induction," Genetics 128, 251-267 (1991).
Beebe, David J., et al., "Physics and Applications of Microfluidics in Biology," Annu. Rev. Biomed., Eng., vol. 4, pp. 261-286 (2002).
Bethe, H.A., "Theory of Diffraction by Small Holes," *The Physical Review*, vol. 66, Nos. 7-8, pp. 163-182 (1944).
Biddiss, Elaine, et al., "Hetergeneous Surface Charge Enhanced Micromixing for Electrokinetic Flows," *Anal. Chem.*, vol. 76, pp. 3208-3213 (2004).
Boppart, S. A., et al., "Forward-imaging instruments for optical coherence tomography," *Optics Letters*, vol. 22, pp. 1618-1620 (1997).
Cao, Jinhua, et al., "Brownian Particle Distribution in Tube Flows," *Proceedings of IMECE04*, vol. 260, pp. 243-252 (2004).
Chen, L., et al. "Role of radiation and surface plasmon polaritons in the optical interactions between a nano-slit and a nano-groove on a metal surface," Optics EXpress, vol. 14, pp. 12629-12636 (2006).
Cheng, Ya, et al., "Microfluidic laser embedded in glass by three-dimensional femtosecond laser microprocessing," *Optics Letters*, vol. 29, No. 17, pp. 2007-2009 (2004).
Chovin, Arnaud, et al., "Fabrication, Characterization, and Far-Field Optical Properties of an Ordered Array of Nanoapertures," Nano Letters, vol. 4, No. 10, pp. 1965-68 (2004).

(56) References Cited

OTHER PUBLICATIONS

Chronis, Nikolas, et al., "Total internal reflection-based biochip utilizing a polymer-filled cavity with a micromirror sidewall," *Miniaturisation for Chemistry, Biology & Bioengineering, Lab Chip*, vol. 4, pp. 125-130 (2004).

Courjon, Daniel, "Near-field Microscopy and near-field optics," *Imperial College Press*, 317 pp. (2003).

Cui et al., "Wavefront Image Sensor Chip," Optics Express 18 (16), 16685-16701, 2010.

Cui, X. et al., "Portable Optical microscope-on-a-chip," *Photonics West*, San Jose, CA Jan. 2006, 8 pp.

Cui, Xiquan, et al., "Lensless high-resolution on-chip optofluidic microscopes for *Caenorhabditis elegans* and cell imaging," Proceedings of the National Academy of Sciences of the Unities States of America, vol. 105, pp. 10670-10675 (2008).

Dahan, M., et al., "Time-gated biological imaging by use of colloidal quantum dots," *Optics Letters*, vol. 26, No. 11, pp. 825-827 (2001).

De Fornel, F., "Evanescent waves from Newtonian optics and Atomic optics," *Springer Series in Optical Sciences*, 270 pages (2001).

Di Mambro et al., "Sharpness limitations in the projection of thin lines by use of the Talbot experiment," J. Opt. Soc. Am. A 21, pp. 2276-2282 (2004).

Drezet, A., et al., "Miniature Plasmonic Wave Plates," Physical Review Letters, vol. 101, pp. 43902-1-043902-4 (Jul. 25, 2008).

Ferguson et al., "Identification and characterization of 22 genes that affect the vulval cell lineages of the nematode *Caenorhabditis elegans*," Genetics 110, 17-72 (1985).

Fowles, G. R., Introduction to Modern Optics, *Dover Publications, Second Ed.*, New York, pp. 57-61 (1989).

Gay, G., et al., "The optical response of nanostructured surfaces and the composite diffracted evanescent wave model," Nat Phys, vol. 2, pp. 262-267 (2006).

Gbur, G., et al., "Achieving superresolution in near-field optical data readout systems using surface plasmons," Applied Physics Letters, vol. 87, p. 191109 (2005).

Genet et al., "Light in tiny holes," Nature 445, 39-46 (2007).

Heng, Xin, et al., "Optofluidic Microscopy," Proceedings of the ICMM 2005 3rd International Conference on Microchannels and Minichannels, pp. 1-6 (2005).

Heng, Xin, "OptoFuidic Microscopy (OFM)" *Biophotonics Group, Caltech, DARPA optofluidic center retreat*, Apr. 1, 2005, 9pp.

Heng, Xin, et al., "Characterization of light collection through a subwavelength aperture from a point source," Optics Express, vol. 14, pp. 10410-10425 (2006).

Heng, Xin, et al., "An Optical Tweezer Actuated, Nanoaperture-grid based Optofluidic Microscope Implimentation Method," Optics EXpress, vol. 15, No. 25, 16367-75 (2007).

Jaiswal, Jyoti K., et al., "Long-term multiple color imaging of live cells using quantum dot biconjugates," Nature Biotechnology, vol. 21, pp. 47-51 (2003).

Kraus, J. D. and Fleisch, D. A., Electromagnetics with Applications (5th Ed), Chapters 4-16 (1999).

Lalanne, P., and Hugonin, J., "Interaction between optical nano-objects at metallo-dielectric interfaces," Nature Physics, vol. 2, p. 551 (2006).

Laux, E., et al., "Plasmonic photon sorters for spectral and polarimetric imaging," Nature Photonics, vol. 2, pp. 161-164 (2008).

Lay, Christophe, et al., "Enhanced microfiltration devices configured with hydrodynamic trapping and a rain drop bypass filtering architecture for microbial cells detection," *Lab on a Chip* 2008, 8:830-833; published as Advanced Article on Apr. 1, 2008 at http://pubs.rsc.org | DOI:10.1039/b800015h, 4 pp.

Lee, Lap Man, et al., "The Application of On-Chip Optofluidic Microscopy for Imaging Giardia lamblia Trophozoites and Cysts," *Biomed Microdevices*, Springer DOI 10.1007/s10544-009-9312-X (2009) 11:951-958.

Leen, J., et al.,"Improved focused ion beam fabrication of near-field apertures using a silicon nitride membrane," Optics Letters, vol. 33, pp. 2827-2829 (2008).

Liang et al., "Objective Measurement of Wave Aberrations of the Human Eye with the Use of a Hartmann-Shack Wave-Front Sensor," J. Opt. Soc. Amer. A-Opt. Image Sci & Vision 11, 1949-1957 (1994).

Liu, H., and Lalanne, P., "Microscopic theory of the eXtraordinary optical transmission," Nature, vol. 452, pp. 728-731 (2008).

Minakawa, K., et al.,"Microchamber Device Equipped with Complementary Metal OXide Semiconductor Optical Polarization Analyzer Chip for Micro Total Analysis System," Jpn. J. Appl. Phys., vol. 48, p. 04C192 (2009).

Ng, R., et al., "Light field photography with a hand-held plenoptic camera," Computer Science Technical Report CSTR, vol. 2 (2005).

Nott, Prabhu R., et al., "Pressure-driven flow of suspensions: simulation and theory," (1994), *J. Fluid Mech.*, vol. 275, pp. 157-199.

Nozokido, Tatsuo, et al., "Scanning Near-Field Millimeter-Wave Microscopy Using a Metal Slit as a Scanning Probe," *IEEE Transactions on Microwave Theory and Techniques*, vol. 49, No. 3, 491-99 (2001).

Ogg et al., "The *C. elegans* PTEN homolog, DAF-18, acts in the insulin receptor-like metabolic signaling pathway," Mol. Cell 2, 887-893 (1998).

Pacifici, D., et al., "All-optical modulation by plasmonic eXcitation of CdSe quantum dots," Nature photonics, vol. 1, pp. 402-406 (2007).

Pacifici, D., et al., "Quantitative determination of optical transmission through subwavelength slit arrays in Ag films: Role of surface wave interference and local coupling between adjacent slits," Physical Review B, vol. 77, p. 115411 (2008).

Pacifici, D., et al., "Universal optical transmission features in periodic and quasiperiodic hole arrays," Optics Express, vol. 16, pp. 9222-9238 (2008).

Platt, B. C. and Shack, R., History and Principles of Shack-Hartmann Wavefront Sensing, *Journal of Refractive Surgery* 17, pp. S573-S577.

Probstein, R. F., "Physicochemical Hydrodynamics," Wiley, 2nd Edition pp. 109-116, 123, 190-197, and 309-310 (2003).

Psaltis, Demetri, et al., "Developing optofluidic technology through the fusion of microfluidics and optics," Nature, vol. 442 (2006).

Schouten, H., et al., "Plasmon-assisted two-slit transmission: Young's experiment revisited," Physical Review Letters, vol. 94, p. 53901 (2005).

Segre, G., et al., "Behavior of macroscopic rigid spheres in Poiseuille flow: Part 1. Determination of local concentration by statistical analysis of particle passages through crossed light beams," J. Fluid Mech., vol. 14, pp. 115-135 (1962).

Segre, G., et al., "Behavior of macroscopic rigid spheres in Poiseuille flow: Part 2. Experimental results and interpretation," J. Fluid Mech., vol. 14, pp. 136-157 (1962).

Seo, Jeonggi, et al., "Disposable integrated microfluidics with Self-aligned planar microlenses," *Sensors and Acutators B*, vol. 99, pp. 615-622 (2004).

Shi, X., et al., "Ultrahigh light transmission through a C-shaped nanoaperture," Optics letters, vol. 28, pp. 1320-1322 (2003).

Spring, Kenneth R., et al., "Introduction to Fluorescence Microscopy," <http://www.microscopyu.com/articles/fluorescence/fluorescenceintro.html> (Aug. 25, 2004).

Stone, H.A., et al., "Engineering Flows in Small Devices: Microfluidics Toward a Lab-on-a-Chip," *Annu. Rev. Fluid Mech.*, vol. 36, pp. 381-411 (2004).

Tearney, G. J., et al., "Scanning single-mode fiber optic catheter-endoscope for optical coherence tomography," Optics Letters, vol. 21, pp. 543-545 (1996).

Thio, T., et al., "Enhanced light transmission through a single subwavelength aperture," Opt. Lett., vol. 26, pp. 1972-1974 (2001).

Thio, T., et al., "Giant optical transmission of sub-wavelength apertures: physics and applications," Nanotechnology, vol. 13, pp. 429-432 (2002).

Thorsen, Todd, et al., "Microfluidic Large-Scale Integration," Science, vol. 298, pp. 580-584 (2002).

Trent et al., "Egg laying defective mutants of the nematode *Caenorhabditis elegans*," Genetics 104, 619-647 (1983).

Ung, B., and Sheng, Y., "Optical surface waves over metallo-dielectric nanostructures: Sommerfeld integrals revisited," Optics Express, vol. 16, pp. 9073-9086 (2008).

(56) References Cited

OTHER PUBLICATIONS

Walker, Glenn, and Beebe, David, "A Passive Pumping Method for Microfluidic Devices," Lab Chip, pp. 131-134 (2002).

Yu, N., et al., "Semiconductor lasers with integrated plasmonic polarizers," Applied Physics Letters, vol. 94, p. 151101, 2009.

Zernike, F., "Phase contrast, a new method for the microscopic observation of transparent objects," Physics 9, pp. 686-698 (1942).

Zheng et al., "Improving Weak-Signal Identification via Predetection Background Suppression by a Pixel-Level, Surface-Wave Enabled Dark-Field Aperture," Optics Letters 35 (15), 2636-2638, 2010.

Zheng, Guoan, et al., "Surface-wave-enabled darkfield aperture: A method for suppressing background during weak signal detection," Proc Natl Acad Sci U S A, vol. 107, No. 20, pp. 9043-9048 (May 2010).

Zhu, Liang, et al., "Filter-based microfluidic device as a platform for immunofluorescent assay of microbial cells," Lab Chip, 2004, vol. 4, pp. 337-341; published as Advanced Article on Apr. 5, 2004 at http://pubs.rsc.org | DOI: 10.1039/b401834f.

United States Patent and Trademark Office (USPTO) Office Action in U.S. Appl. No. 12/398,098 dated on Jul. 1, 2013.

United States Patent and Trademark Office (USPTO) Notice of Allowance in U.S. Appl. No. 13/229,741 dated on Apr. 24, 2013.

United States Patent and Trademark Office (USPTO) Notice of Allowance in U.S. Appl. No. 13/344,523 dated on Nov. 6, 2013.

Beam Steering Using Liquid Crystals, Boulder Nonlinear Systems, downloaded from the Internet at http://www.bnonlinear.com/papers/LCBeamSteering.pdf, May 8, 2001, 4 pages.

Types of confocal microscopy, downloaded from the Internet at http://www.mikriskipie.org/2008/01/26/types-of-confocal-microscopy/14/ on Sep. 10, 2010, 1 page.

Graydon, (Oct. 2010) "Imaging Phase Sensor on a Chip," *Nature Photonics*, 4(10):p. 668.

Pang, Shuo, et al., (2011) "Fluorescence microscopy imaging with a Fresnel zone plate array based optofluidic microscope, " *Lab on a Chip*, 11:3698-3702.

Ren et al., (2012) "Quantitative Surface Normal Measurement by a Wavefront Camera," *Optics Letters*, 37(2):199-201.

Wu (2007) "Harmonically Matched Grating-Based Full-Field Quantitative High-Resolution Phase Microscope for Observing Dynamics of Transparent Biological Samples," *Optics Express*, 15(26):18141-55.

Wu, J., Cui, X., Lee, L. M., and Yang, C., (2008) "The application of Fresnel zone plate based projection in optofluidic microscopy," *Opt. Exp*. 16(20):15595-15602.

Zheng et al., (2010) "Pixel level optical-transfer-function design based on the surface-wave-interferometry aperture," *Optics Express*, 18(16):16499-16506.

\* cited by examiner

US 8,660,312 B2

QUANTITATIVE DIFFERENTIAL INTERFERENCE CONTRAST (DIC) DEVICES FOR COMPUTED DEPTH SECTIONING

CROSS-REFERENCES TO RELATED APPLICATIONS

This is a non-provisional application that claims benefit of the filing date of U.S. Provisional Patent Application No. 61/205,487 entitled "Quantitative differential interference contrast (DIC) microscopy and its computed depth sectioning ability" filed on Jan. 21, 2009. That provisional application is hereby incorporated by reference in its entirety for all purposes.

This non-provisional application is related to the following co-pending and commonly-assigned patent applications, which are hereby incorporated by reference in their entirety for all purposes:
- U.S. patent application Ser. No. 11/125,718 entitled "Optofluidic Microscope Device" filed on May 9, 2005.
- U.S. patent application Ser. No. 11/686,095 entitled "Optofluidic Microscope Device" filed on Mar. 14, 2007.
- U.S. patent application Ser. No. 11/743,581 entitled "On-chip Microscope/Beam Profiler based on Differential Interference Contrast and/or Surface Plasmon Assisted Interference" filed on May 2, 2007.
- U.S. patent application Ser. No. 12/398,098 entitled "Methods of Using Optofluidic Microscope Devices" filed Mar. 4, 2009.
- U.S. patent application Ser. No. 12/398,050 entitled "Optofluidic Microscope Device with Photosensor Array" filed on Mar. 4, 2009.
- U.S. patent application Ser. No. 12/638,518 entitled "Techniques for Improving Optofluidic Microscope Devices" filed on Dec. 15, 2009.
- U.S. patent application Ser. No. 12/435,165 entitled "Quantitative Differential Interference Contrast (DIC) Microscopy and Photography based on Wavefront Sensors" filed May 4, 2009.

BACKGROUND OF THE INVENTION

Embodiments of the present invention generally relate to quantitative differential interference contrast (DIC) devices with wavefront sensors. More specifically, certain embodiments relate to quantitative DIC devices with wavefront sensors used in applications such as microscopy or photography, and that are adapted to compute depth sectioning of specimens and other objects.

DIC microscopes render excellent contrast for optically transparent biological samples without the need of introducing exogenous contrast agents into the samples. Due to the noninvasive nature, DIC microscopes are widely used in biology laboratories.

Conventional DIC microscopes and other conventional DIC devices typically operate by first creating two identical illumination light fields exploiting polarization selection. FIG. 1 is a schematic drawing of a conventional DIC device 10 that operates by interfering slightly displaced duplicate image light fields of polarized light. The conventional DIC device 10 includes an illumination source 20 providing polarized light to an object 30. As illustrated, the light fields are transmitted through the object 30 and are laterally displaced with respect to each other along the x-direction. A net phase lag (typically $\pi/2$) is then introduced on one of the transmitted image light fields. The two light fields are allowed to interfere with each other at the image plane 40. More simply, the process is equivalent to duplicating the transmitted image light field, laterally displacing a copy slightly and detecting the interference of the two light fields at image plane 40.

Mathematically, this implies that the observed DIC intensity image 42 from the conventional DIC device 10 with a magnification factor of M is given by Eq. (1):

$$I_{DIC}(x, y) = |\psi_{DIC}(x, y)|^2 \qquad (1)$$
$$= B(x, y) + C(x, y) * \sin\left(\begin{array}{c}\arg(\psi(x-\Delta/2, y)) - \\ \arg(\psi(x+\Delta/2, y))\end{array}\right)$$
$$\approx B(x, y) + C(x, y) * \left(\begin{array}{c}\arg(\psi(x-\Delta/2, y)) - \\ \arg(\psi(x+\Delta/2, y))\end{array}\right)$$

where $B(x, y) = |(\psi(x-\Delta/2,y))|^2 + |(\psi(x+\Delta/2,y))|^2$, $C(x, y) = 2|(\psi(x-\Delta/2,y))||(\psi(x+\Delta/2,y))|$, and $\psi(x, y)$ is the image wavefront as relayed by the microscope for each light field, $\psi_{DIC}(x, y)$ is the DIC image wavefront, and $\Delta = Ma$ is the relative displacement of the images associated with the light fields. The last expression in Eq. (1) is valid only in situations where the phase difference is small.

However, conventional DIC devices have several limitations. One major limitation is that conventional DIC devices translate phase variations into amplitude (intensity) variations. As shown in Eq. (1), the DIC intensity image, $I_{DIC}(x,y)$ is a sine function of the differential phase so that the phase information cannot be interpreted directly from the intensity of the DIC image. Also, the $B(x,y)$ and $C(x,y)$ terms both contain amplitude information so that the DIC image contains entangled amplitude and phase information. Therefore, phase variations cannot be easily disentangled from amplitude (intensity) variations that arise from absorption and/or scattering by an object. In other words, conventional DIC devices do not distinguish between the effects of absorption and phase variation. As a consequence of this entanglement of amplitude and phase information and nonlinear phase gradient response, conventional DIC devices are inherently qualitative and do not provide quantitative phase measurements Another limitation of conventional DIC devices is that they use polarized light and depend on the polarization in their phase-imaging strategies. Since polarized light must be used, conventional DIC devices generate images of birefringent objects (e.g., potato starch storage granules) that typically suffer from significant artifacts.

BRIEF SUMMARY OF THE INVENTION

Embodiments of the present invention relate to methods of using a quantitative DIC device(s) to compute depth sections of an object. An object introduced into the quantitative DIC device alters a light field and induces an image wavefront having an amplitude and phase gradient. The light detector at the back of the wavefront sensor measures the distribution of light passing through structured apertures in the wavefront sensor. The wavefront sensor uses the light distribution to measures separately the amplitude and phase gradient of the wavefront in two orthogonal directions. The quantitative DIC device numerically reconstructs the image wavefront from the amplitude and phase gradient, and computationally propagates the reconstructed wavefront to planes at different depths through the thickness of the object.

One embodiment is directed to a method for computing depth sectioning of an object using a quantitative differential interference contrast device having a wavefront sensor with one or more structured apertures, a light detector and a transparent layer between the one or more structured apertures and the light detector. The method comprises receiving light by the light detector through the one or more structured apertures. The method further comprises measuring an amplitude of an image wavefront based on the received light measuring a phase gradient in two orthogonal directions of the image wavefront based on the received light. Then, the processor reconstructs the image wavefront using the measured amplitude and phase gradient and propagates the reconstructed wavefront to a first plane intersecting an object at a first depth.

Another embodiment is directed to a wavefront sensor comprising an aperture layer having one or more structured apertures, a light detector and a transparent layer between the aperture layer and the light detector. The light detector measures the amplitude of the wavefront and the phase gradient in two orthogonal directions based on the light received through the structured apertures.

Another embodiment is directed to a quantitative DIC device comprising a wavefront sensor and a processor communicatively coupled to the wavefront sensor. The wavefront sensor comprises an aperture layer having one or more structured apertures, a light detector and a transparent layer between the aperture layer and the light detector. The light detector measures the amplitude of the wavefront and the phase gradient in two orthogonal directions based on the light received through the structured apertures. The processor reconstructs the wavefront using the measured amplitude and phase gradient.

These and other embodiments of the invention are described in further detail below.

BRIEF DESCRIPTION OF THE DRAWINGS

FIG. 6($b$) is a schematic drawing of a side view of components of a quantitative DIC device having a SAI wavefront sensor, according to an embodiment of the invention.

FIG. 6($c$) is a schematic drawing of a side view of components of a quantitative DIC device having a SAI wavefront sensor, according to an embodiment of the invention.

FIG. 7($a$)(2) is a schematic drawing of a perspective view of a two-dimensional structured aperture in the form of a 'plus' sign configuration, according to an embodiment of the invention.

FIGS. 7($b$), 7($c$), and 7($d$) are images taken by a scanning electron microscope of two-dimensional structured apertures, according to embodiments of the invention.

FIG. 10($b$) is a schematic drawing of a top view of components of a quantitative DIC device having an OFM wavefront sensor, according to an embodiment of the invention.

FIG. 15($b$) is a top view of components of the wavefront sensor in FIG. 15($a$), according to an embodiment of the invention.

FIG. 15($c$) is a sectional view of components of the wavefront sensor in FIG. 15($a$) through the center of structured aperture, according to an embodiment of the invention.

FIG. 16($b$) is an image based on phase gradient in the x direction taken of a starfish embryo using a quantitative DIC device having an SAI wavefront sensor, according to an embodiment of the invention.

FIG. 16($c$) is an image based on phase gradient in the y direction taken of a starfish embryo using a quantitative DIC device having an SAI wavefront sensor, according to an embodiment of the invention.

FIGS. 16($d$), 16($e$) and 16($f$) showcase some of the unwrapping algorithms when applied to the raw amplitude, differential phase x and differential phase y data of FIGS. 16($a$), 16($b$) and 16($c$), according to embodiments of the invention.

FIG. 17($b$) is an image of potato starch storage granules in immersion oil taken by a conventional DIC microscope.

FIG. 17($c$) is an intensity image of potato starch storage granules in immersion oil taken by a quantitative DIC device in a microscope system, according to an embodiment of the invention.

FIG. 17($d$) is an artifact-free x-direction phase image of potato starch storage granules in immersion oil taken by a quantitative DIC device in a microscope system, according to an embodiment of the invention.

FIG. 17($e$) is an artifact-free y-direction phase image of potato starch storage granules in immersion oil taken by a quantitative DIC device in a microscope system, according to an embodiment of the invention.

DETAILED DESCRIPTION OF THE INVENTION

Embodiments of the present invention will be described below with reference to the accompanying drawings. Some embodiments include a simple and quantitative DIC device with a wavefront sensor that can be used in applications such as microscopy, photography, or other imaging applications.

Wavefront sensors of embodiments of the invention can be in any suitable form. For example, the wavefront sensor can be in the form of a single pixel (element) wavefront sensor. In another example, the wavefront sensor can be in the form of a one dimensional wavefront sensor array having sensor elements (e.g., pixels) located along a single direction. In another example, the wavefront sensor can be in the form of a two-dimensional wavefront sensor array comprising sensor elements located along two orthogonal directions.

In general, quantitative DIC devices of embodiments of the invention provide advantages because they can separately measure the amplitude and phase gradient of an image wavefront in two orthogonal directions. With this information, the quantitative DIC device has sufficient data to numerically reconstruct an image wavefront and propagate it to other planes.

Quantitative DIC devices of embodiments of the invention also provide advantages because they do not require polarized light as part of their imaging technique. Since these quantitative DIC devices are not dependent on the polarization of the light (illumination), these devices can use unpolarized light to generate artifact-free DIC images for both birefringent and homogenous objects. Also, an ordinary light source can be used such as the light source used in a conventional microscope. Another advantage of the quantitative DIC devices of embodiments of the invention is that they integrate DIC functionality onto a simple wavefront sensor. This integration is advantageous over conventional DIC devices which use bulky optical elements to provide DIC functionality. For this reason, embodiments of the present invention are more compact, less expensive, and simpler in use and design than conventional DIC devices.

Figure 1:
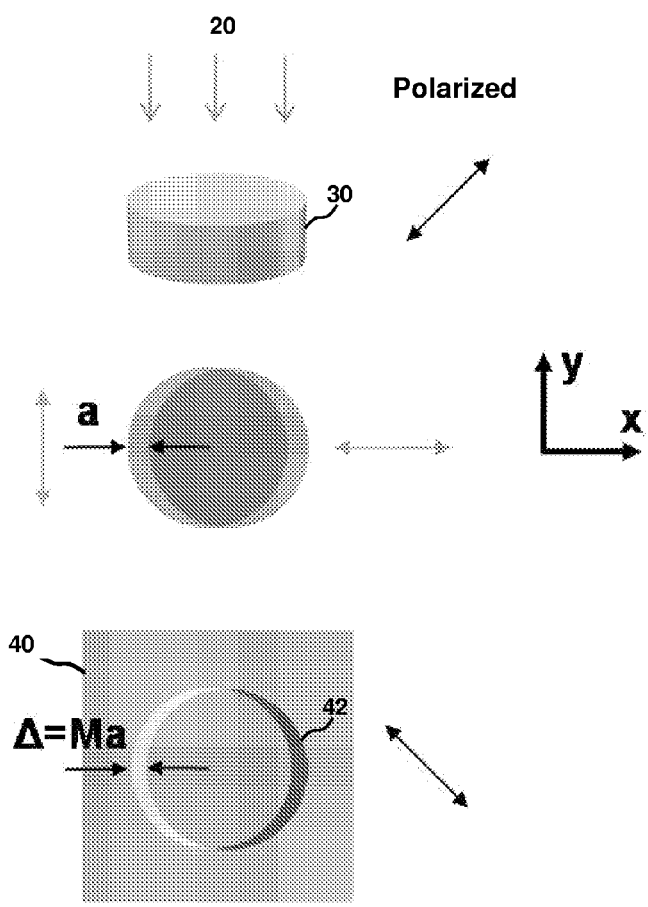
FIG. 1. is a schematic drawing of a conventional DIC device.
Figure 2:
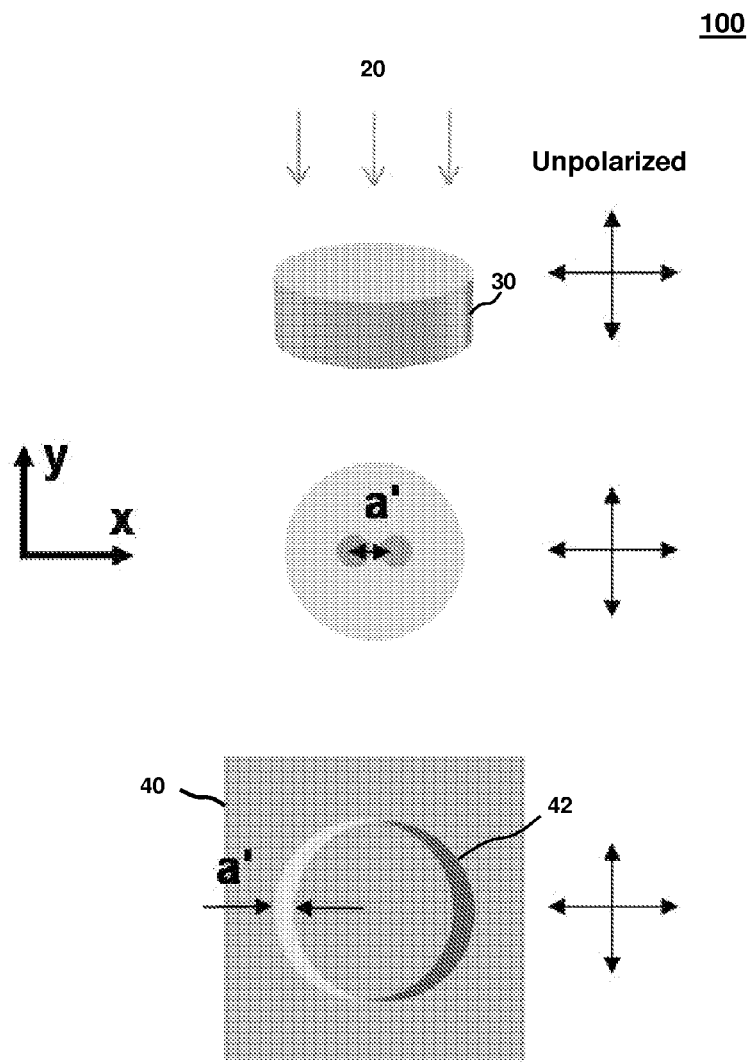
FIG. 2 is schematic drawing of a quantitative DIC device, according to an embodiment of the invention.

Quantitative DIC devices of embodiments of the invention operate by selectively combining and interfering light fields of unpolarized light at two adjacent points as illustrated in FIG. 2. FIG. 2 is schematic drawing of a quantitative DIC device 100, according to an embodiment of the invention. The quantitative DIC device 100 includes an illumination source 20 providing unpolarized light to an object 30. In this illustrated embodiment, the quantitative DIC device 100 employs a phase comparison that selectively combines and interferes the light fields of unpolarized light at two adjacent points of the image with a separation a. The quantitative DIC device 100 uses the phase comparison to generate the image 42 of the object 30 at the image plane 40. Quantitative DIC devices employing this phase comparison can separately measure the amplitude and phase gradient of the light scattered by, or transmitted through, the object 30.

I. Quantitative DIC Device Configurations

Three configurations of quantitative DIC devices are described below. The first configuration includes a quantitative DIC device with a single pixel wavefront sensor. In this configuration, raster scanning can be employed to measure two-dimensional data about the image wavefront. The second configuration includes a two-dimensional wavefront sensor array which can measure the two-dimensional data about the image wavefront at the same time, without the need for raster scanning. The first and second configurations use a wavefront relay system to project the image wavefront from the object to the wavefront sensor. The third configuration eliminates the wavefront relay system of the previous two configurations.

In some embodiments, the quantitative DIC devices of these configurations do not depend on the polarization of light as part of their imaging method. These quantitative DIC devices can generate artifact-free DIC images, even for birefringence objects, if unpolarized light is used.

A. First Configuration

Figure 3:
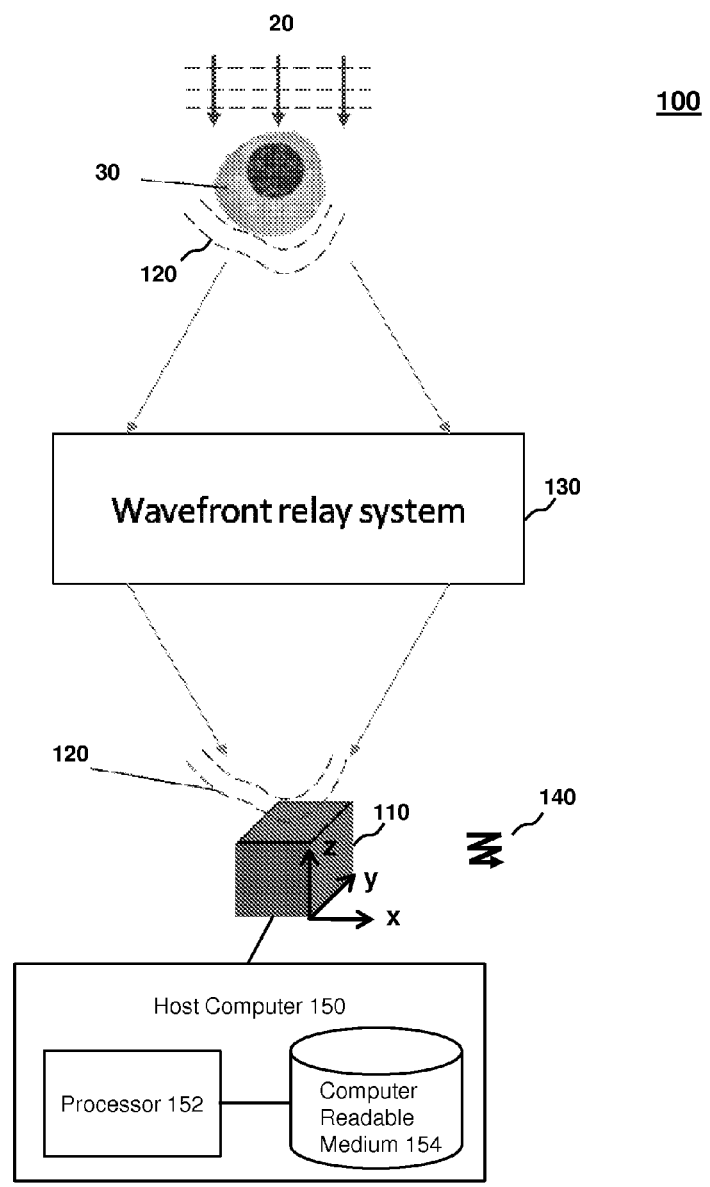
FIG. 3 is schematic drawing of a side view of components of a quantitative DIC device in a first configuration, according to an embodiment of the invention.

FIG. 3 is a schematic drawing of a side view of components of a quantitative DIC device 100 in a first configuration, according to an embodiment of the invention. In this configuration, the quantitative DIC device 100 includes a single pixel wavefront sensor 110. An illumination source 20 provides light to an object 30 being imaged by the quantitative DIC device 100. The object 30 modulates or otherwise alters the light and induces an image wavefront 120. The quantitative DIC device 100 also includes a wavefront relay system 130 (e.g., one or more lenses) in communication with the single pixel wavefront sensor 110. The wavefront relay system 130 projects or otherwise relays the image wavefront 120 generated by the object 30 onto the single pixel wavefront sensor 110. The single pixel wavefront sensor 110 measures the local intensity and/or slope of the projected image wavefront 120 induced by a point of the object 30, which conjugates with the single pixel wavefront sensor 110.

The quantitative DIC device 100 further includes a raster scanning device 140 for scanning the object 30 or scanning the single pixel wavefront sensor 110 to generate two-dimensional maps of the local intensity and/or slope of the image wavefront 120 induced by the object 30. The quantitative DIC device 100 further includes a host computer 150 having a processor 152 in communication with a computer readable medium (CRM) 154. The host computer 150 is in communication with the single pixel wavefront sensor 110 to receive wavefront data. One or more components of the quantitative DIC device 100 can be located within a body, which can be a multi-layer structure or a single, monolithic structure.

The quantitative DIC device 100 measures the two-dimensional amplitude and measures the phase gradient in two orthogonal directions of the image wavefront 120 based on the measured intensity distribution. The total transmission of the interference is proportional to the average image intensity at the aperture plane. The offsets ($\Delta s$ and $\Delta t$) of the zero-order interference spot are related to the wavelength-normalized phase gradients ($\theta_x$ and $\theta_y$) at the aperture, respectively, through the spacer (transparent layer) thickness (H) and refractive index (n) as:

$$\theta_x(x, y) = \frac{\lambda}{2\pi} \frac{\partial \varphi(x, y)}{\partial x} \approx n\frac{\Delta s}{D} \qquad (2)$$

$$\theta_y(x, y) = \frac{\lambda}{2\pi} \frac{\partial \varphi(x, y)}{\partial x} \approx n\frac{\Delta t}{D}. \qquad (3)$$

Using an unwrapping method, the quantitative DIC device 100 can numerically reconstruct the two-dimensional image wavefront 120 associated with the object 30 using the measured two-dimensional amplitude and phase gradient information. The quantitative DIC device 100 can then computationally propagate the image wavefront 120 to one or more z-planes at different depths through the thickness of the object 30. The quantitative DIC device 100 can generate an intensity image, a phase gradient image in the x-direction, and a phase gradient image in the y-direction of the object 30, a reconstructed image, and propagated two dimensional images at different depths through the thickness of the object 30. In some cases, the two dimensional images are cross-sectional images of the object 30. The quantitative DIC device 100 can also combine the two-dimensional wavefront data to generate three-dimensional data and images of the object 30. The computing depth sectioning method will be described in further detail in following sections.

An illumination source 20 can refer to any suitable device or other source of light such as ambient light. The light provided by illumination source 20 can be of any suitable wavelength and intensity. Also, the light can include polarized and/or unpolarized light. In embodiments where unpolarized light is used, the quantitative DIC device 100 can generate artifact-free DIC images of birefringence specimens or other objects 30 in samples. Suitable illumination sources 20 are naturally and commercially available. In some embodiments, the illumination source 20 can be a component of the quantitative DIC device 100. In other embodiments, the illumination source can be a separate from the quantitative DIC device 100.

An illumination source 20 can be placed in any suitable location and positioned in any suitable direction to provide appropriate light to the object 30. In some embodiments, multiple illumination sources 20 provide light in one or more directions. For example, a camera system including a quantitative DIC device may have a first illumination source 20 that provides light in a direction from the wavefront sensor to the object 30 such as from a flash and a second illumination source 20 that provides light in another direction. In other embodiments, a single illumination source provides light in a single direction. For example, a microscope system comprising a quantitative DIC device 100 may have a single illumination source 20 positioned to provide light in the negative z-direction.

Figure 4:
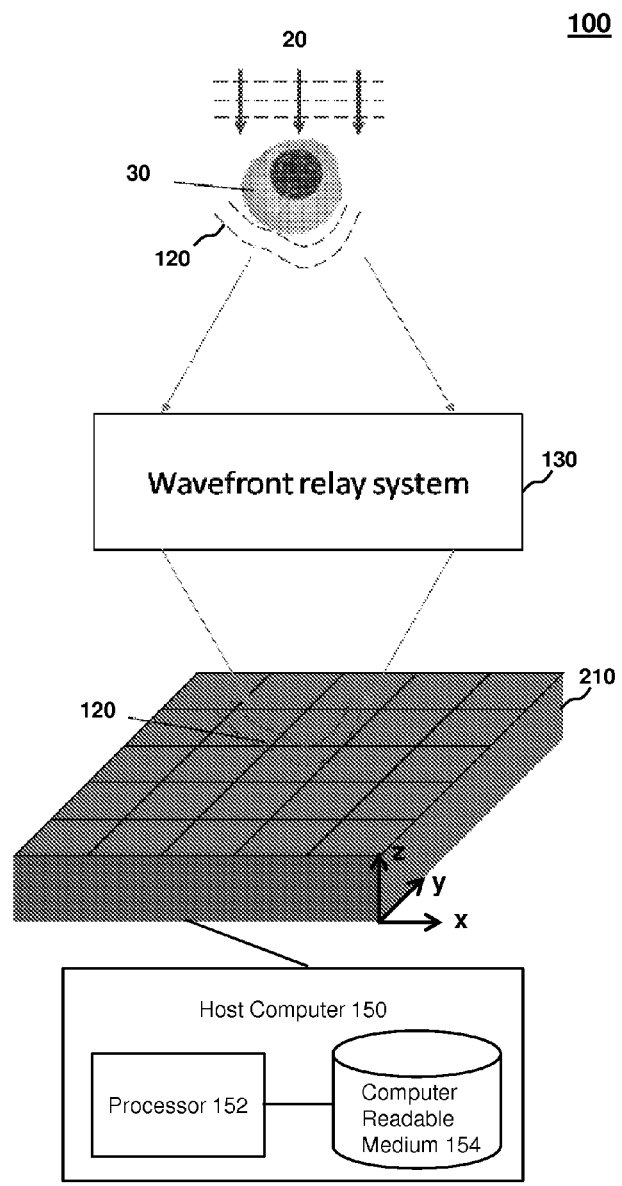
FIG. 4 is a schematic drawing of a side view of components of a quantitative DIC device in a second configuration, according to an embodiment of the invention.
Figure 5:
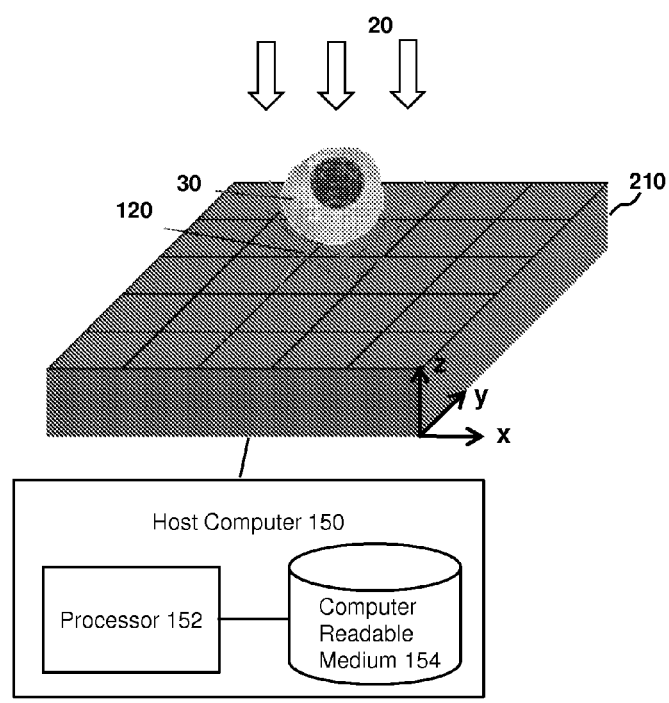
FIG. 5 is a schematic drawing of a side view of components of a quantitative DIC device in a third configuration, according to an embodiment of the invention.

A wavefront relay system 130 can refer to a device or combination of devices configured to relay (e.g., project) the image wavefront 120 induced by the object 30 onto a wavefront sensor such as the single pixel wavefront sensor 110 in FIG. 3 or the wavefront sensor array 210 shown in FIGS. 4 and 5. In one example, a wavefront relay system 130 includes one or more lenses. The light may be relayed in any suitable manner. In FIG. 3, the wavefront relay system 130 projects the image wavefront 120 from the object 30 onto a single pixel wavefront sensor 110.

A raster scanning device 140 can refer to any suitable device for raster scanning the object 30 or raster scanning the wavefront sensor. The raster scanning device 140 can be a component of the quantitative DIC device 100 in some embodiments and can be a separate device in other embodiments.

In the illustrated embodiment, the host computer 150 is a component of the quantitative DIC device 100. In other embodiments, the host computer 150 can be a separate device. Although the processor 152 and CRM 154 are shown as components of the quantitative DIC device 100, in other embodiments the processor 152 and/or CRM 154 can be components of the wavefront sensor.

A processor (e.g., a microprocessor) can refer to any suitable device for processing the functions of the quantitative DIC device 100. In the illustrated embodiment, the processor 150 receives signals with wavefront data associated with the intensity distribution and/or slope data of the image wavefront 120 measured by the single pixel wavefront sensor 110. The wavefront data may include a two-dimensional map of the intensity distribution and/or slope of the image wavefront 120 measured by the single pixel wavefront sensor 110 by employing the raster scanning device 140, the amplitude and phase gradient data associated with the image wavefront 120, the wavelength(s) of the light, and/or other information about the light received by the single pixel wavefront sensor 110. The processor 150 executes code stored on the CRM 154 to perform some of the functions of the quantitative DIC device 100. These functions include interpreting the light distribution and/or slope data measured by the single pixel wavefront sensor 110, measuring the center of a projection through a structured aperture, separating the projections from structured apertures, determining offsets of the projections or the focal points, determining the amplitude and phase gradient of the image wavefront 120 in two orthogonal directions using the light distribution data, reconstructing the image wavefront using the amplitude and phase gradient data in two orthogonal directions, propagating the reconstructed wavefront from the detector z plane to one or more z planes, generating one or more two-dimensional images based on intensity, phase gradient in the x-direction, phase gradient in the y-direction, the reconstructed wavefront, and/or the propagated wavefronts, combining two-dimensional image data to generate three-dimensional data and images of the object 30, displaying one or more images of the object 30, and other functions associated with computed depth sectioning and image processing.

A CRM 154 can refer to a memory that stores data and may be in any suitable form including a memory chip, etc. The CRM 154 stores the code for performing some functions of the quantitative DIC device 100. The code is executable by the processor 152. In one embodiment, the CRM 154 comprises a) code for interpreting the light distribution data received from the single pixel wavefront sensor 110, b) code for generating local slope data from the light distribution data, c) code for determining the amplitude of the image wavefront 120, and determining the phase gradient of the image wavefront 120 in two orthogonal directions using the light distribution data, d) code for reconstructing the image wavefront using the amplitude data and the phase gradient data in two orthogonal directions, e) code for propagating the reconstructed wavefront from the detector z plane to one or more z planes, f) code for generating one or more two-dimensional images based on intensity, phase gradient in the x-direction, phase gradient in the y-direction, the reconstructed wavefront, and/or the propagated wavefronts, and g) code for combining two-dimensional image data to generate three-dimensional data and images of the object 30, h) code for displaying one or more images of the object 30, and i) any other suitable code for computed depth sectioning and image processing. The CRM 154 may also include code for performing any of the signal processing or other software-related functions that may be created by those of ordinary skill in the art. The code may be in any suitable programming language including C, C++, Pascal, etc.

Although not shown, the quantitative DIC device 100 may also include a display communicatively coupled to the processor 152. Any suitable display may be used. In one embodiment, the display may be a part of the quantitative DIC device 100. The display may provide information such as the image of the object 30 to a user of the quantitative DIC device 100. In addition, the quantitative DIC device 100 may also have an input device communicatively coupled to the processor 152.

B. Second Configuration

FIG. 4 is a schematic drawing of a side view of components of a quantitative DIC device 100 in a second configuration, according to an embodiment of the invention. The second configuration of the quantitative DIC device 100 includes a two-dimensional wavefront sensor array 210 of sensor elements for measuring two-dimensional data about the image wavefront 120 in a single snapshot reading without the need of raster scanning.

In the illustrated example, the quantitative DIC device 100 includes an illumination source 20 for providing light to an object 30 being imaged. The object 30 modulates or otherwise alters the light and induces an image wavefront 120. Although a single illumination source 20 providing light in a single direction is shown in the illustrated embodiment, multiple illumination sources can be used providing light in one or more directions.

The quantitative DIC device 100 also includes a wavefront relay system 130 in communication with the wavefront sensor array 210. The wavefront relay system 130 projects or otherwise relays the image wavefront 120 generated by the object 30 onto the wavefront sensor array 210. Each sensor element (pixel) of the wavefront sensor array 210 measures the local intensity and slope of the image wavefront 120 induced by a point of the object 30 which conjugates with the sensor element (pixel). In this case, the quantitative DIC device 100 naturally measures two-dimensional maps of the local intensity and slope of the image wavefront 120 modulated by the object 30 at the same time. Although a raster scanning device is not shown in the illustrated embodiment, another embodiment can include a raster scanning device 140 to raster scan the object 30 or the wavefront sensor array 210 to form more densely sampled images.

The quantitative DIC device 100 also includes a host computer 150 having a processor 152 in communication with a computer readable medium (CRM) 154. The host computer 150 is in communication with the wavefront sensor array 210 to receive wavefront data. One or more components of the quantitative DIC device 100 can be located within a body, which can be a multi-layer structure or a single, monolithic structure.

The quantitative DIC device 100 measures the two-dimensional amplitude and phase gradient of the image wavefront 120 based on the measured intensity distribution using Eqs. (2) and (3). Using an unwrapping method, the quantitative DIC device 100 can reconstruct the two-dimensional image wavefront 120 associated with the object 30 using the measured two-dimensional amplitude and phase gradient information. The quantitative DIC device 100 can computationally propagate the reconstructed image wavefront 120 to one or more z-planes at different depths through the thickness of the object 30. The quantitative DIC device 100 can generate an intensity image, a phase gradient image in the x-direction, and a phase gradient image in the y-direction of the object 30, a reconstructed image, and propagated two dimensional images at different depths through the thickness of the object 30. In some cases, the two dimensional images are cross-sectional images of the object 30. The quantitative DIC device 100 can also combine the two-dimensional wavefront data to generate three-dimensional data and images of the object 30. The computing depth sectioning method will be described in further detail in following sections.

In the illustrated embodiment, the host computer 150 is a component of the quantitative DIC device 100. In other embodiments, the host computer 150 can be a separate device. Although the processor 152 and CRM 154 are shown as components of the quantitative DIC device 100, in other embodiments the processor 152 and/or CRM 154 can be components of the wavefront sensor.

In the illustrated embodiment, the processor 150 receives signals with wavefront data associated with the intensity distribution and slope of the image wavefront 120 measured by the wavefront sensor array 210. The wavefront data may include the two-dimensional map of the intensity distribution and slope of the image wavefront 120 measured by the wavefront sensor array 210, the amplitude and phase gradient information associated with the image wavefront 120, the wavelength(s) of the light, and/or other information about the light received by the wavefront sensor array 210. The processor 150 executes code stored on the CRM 154 to perform some of the functions of the quantitative DIC device 100 such as interpreting the intensity distribution and/or slope data measured by wavefront sensor array 210, generating amplitude and phase gradient information associated with the image wavefront 120 induced by the object 30, reconstructing an image wavefront 120 using the amplitude and phase gradient information, computing depth sectioning of the object by numerically propagating the image wavefront 120 back to multiple z-planes through the depth of the object 30 to generate two-dimensional image information about the object 30, and generating three-dimensional information about the object 30 from the two-dimensional information multiple z-planes of the object 30.

A CRM 154 can refer to any computer readable medium (e.g., memory) that stores data and may be in any suitable form including a memory chip, etc. The CRM 154 stores the code for performing some functions of the quantitative DIC device 100. The code is executable by the processor. In one embodiment, the CRM 154 includes a) code for interpreting the light distribution data received from the wavefront sensor array 210, b) code for generating local slope data from the light distribution data, c) code for determining the amplitude of the image wavefront 120, and determining the phase gradient of the image wavefront 120 in two orthogonal directions using the light distribution data, c) code for reconstructing the image wavefront using the amplitude and phase gradient data in two orthogonal directions, d) code for propagating the reconstructed wavefront from the detector z plane to one or more z planes, e) code for generating one or more two-dimensional images based on intensity, phase gradient in the x-direction, phase gradient in the y-direction, the reconstructed wavefront, and/or the propagated wavefronts, and f) code for combining two-dimensional image data to generate three-dimensional data and images of the object 30, g) code for displaying one or more images of the object 30, and h) any other suitable code for computed depth sectioning and image processing. The CRM 154 may also include code for performing any of the signal processing or other software-related functions that may be created by those of ordinary skill in the art. The code may be in any suitable programming language including C, C++, Pascal, etc.

Although not shown, the quantitative DIC device 100 may also include a display communicatively coupled to the processor 152. Any suitable display may be used. In one embodiment, the display may be a part of the quantitative DIC device 100. The display may provide information such as the image of the object 30 to a user of the quantitative DIC device 100.

C. Third Configuration

FIG. 5 is a schematic drawing of a side view of components of a quantitative DIC device 100 in a third configuration, according to an embodiment of the invention. The third configuration of the quantitative DIC device 100 eliminates the wavefront relay system 130 included in the first and second configurations. In the illustrated embodiment, the quantitative DIC 100 includes a two-dimensional wavefront sensor array 210 of sensor elements for measuring two-dimensional data about the image wavefront 120 at the same time. In another embodiment, a quantitative DIC 100 in the third configuration comprises a single pixel wavefront sensor 110 and a raster scanning device 140. In yet another embodiment, a quantitative DIC 100 in the third configuration comprises a one dimensional OFM wavefront sensor array that uses an optofluidic microscope (OFM) scanning scheme shown in FIGS. 10(a) and 10(b). In this embodiment, the sensor elements detect time varying data as the object 30 passes through a fluid channel in the form of line scans. The line scans are compiled to generate two-dimensional data.

In the illustrated example shown in FIG. 5, the quantitative DIC device 100 includes an illumination source 20 providing light to an object 30 being imaged. The object 30 modulates or otherwise alters the light, which induces the image wavefront 120. Although a single illumination source 20 providing light in a single direction is shown in the illustrated embodiment, multiple illumination sources can be used providing light in one or more directions.

The quantitative DIC device 100 also includes a host computer 150 having a processor 152 in communication with a computer readable medium (CRM) 154. The host computer 150 is in communication with the wavefront sensor array 210 to receive wavefront data.

Each sensor element (pixel) of the wavefront sensor array 210 measures the local intensity and slope of the image wavefront 120 induced by a point of the object 30 which conjugates with the sensor element (pixel). In this case, the quantitative DIC device 100 naturally measures two-dimensional maps of the local intensity and slope of the image wavefront 120 modulated by the object 30 at the same time. Although a raster scanning device is not shown in the illustrated embodiment, another embodiment can include a raster scanning device 140 to raster scan the object 30 or the wavefront sensor array 210 to form more densely sampled images.

The quantitative DIC device 100 measures the two-dimensional amplitude and phase gradient of the image wavefront 120 based on the measured intensity distribution using Eqs. (2) and (3). Using an unwrapping method, the quantitative DIC device 100 can reconstruct the two-dimensional image wavefront 120 associated with the object 30 using the measured two-dimensional amplitude and phase gradient information. The quantitative DIC device 100 can computationally propagate the reconstructed image wavefront 120 to one or more z-planes at different depths through the thickness of the object 30. The quantitative DIC device 100 can generate an intensity image, a phase gradient image in the x-direction, and a phase gradient image in the y-direction of the object 30, a reconstructed image, and propagated two dimensional images at different depths through the thickness of the object 30. In some cases, the two dimensional images are cross-sectional images of the object 30. The quantitative DIC device 100 can also combine the two-dimensional wavefront data to generate three-dimensional data and images of the object 30. The computing depth sectioning method will be described in further detail in following sections.

In the illustrated embodiment, the host computer 150 is a component of the quantitative DIC device 100. In other embodiments, the host computer 150 can be a separate device. Although the processor 152 and CRM 154 are shown as components of the quantitative DIC device 100, in other embodiments the processor 152 and/or CRM 154 can be components of the wavefront sensor.

In the illustrated embodiment, the processor 150 receives signals with wavefront data associated with the intensity distribution and slope of the image wavefront 120 measured by the wavefront sensor array 210. The wavefront data may include the two-dimensional map of the intensity distribution and slope of the image wavefront 120 measured by the wavefront sensor array 210, the amplitude and phase gradient information associated with the image wavefront 120, the wavelength(s) of the light, and/or other information about the light received by the wavefront sensor array 210. In some embodiments, the wavefront data further includes time varying information from an OFM wavefront sensor which can be in the form of line scans. The processor 150 executes code stored on the CRM 154 to perform some of the functions of the quantitative DIC device 100 such as interpreting the intensity distribution and/or slope data measured by wavefront sensor array 210, generating amplitude and phase gradient information associated with the image wavefront 120 induced by the object 30, reconstructing an image wavefront 120 using the amplitude and phase gradient information, computing depth sectioning of the object by numerically propagating the image wavefront 120 back to multiple z-planes through the depth of the object 30 to generate two-dimensional image information about the object 30, and generating three-dimensional information about the object 30 from the two-dimensional information multiple z-planes of the object 30.

A CRM 154 can refer to any computer readable medium (e.g., memory) that stores data and may be in any suitable form including a memory chip, etc. The CRM 154 stores the code for performing some functions of the quantitative DIC device 100. The code is executable by the processor. In one embodiment, the CRM 154 comprises a) code for interpreting the light distribution data received from the wavefront sensor array 210, b) code for generating local slope data from the light distribution data, c) code for determining the amplitude of the image wavefront 120, and determining the phase gradient of the image wavefront 120 in two orthogonal directions using the light distribution data, d) code for reconstructing the image wavefront using the amplitude of the image wavefront 120, and determining the phase gradient data in two orthogonal directions, e) code for propagating the reconstructed wavefront from the detector z plane to one or more z planes, f) code for generating one or more two-dimensional images based on intensity, phase gradient in the x-direction, phase gradient in the y-direction, the reconstructed wavefront, and/or the propagated wavefronts, and g) code for combining two-dimensional image data to generate three-dimensional data and images of the object 30, h) code for displaying one or more images of the object 30, and i) any other suitable code for computed depth sectioning and image processing. The CRM 154 may also include code for performing any of the signal processing or other software-related functions that may be created by those of ordinary skill in the art. The code may be in any suitable programming language including C, C++, Pascal, etc.

Although not shown, the quantitative DIC device 100 may also include a display communicatively coupled to the processor 152. Any suitable display may be used. In one embodiment, the display may be a part of the quantitative DIC device 100. The display may provide information such as the image of the object 30 to a user of the quantitative DIC device 100.

In addition, the quantitative DIC device 100 of some embodiments may also include a body which incorporates one or more components of the quantitative DIC device 100. The body can be a multi-layer structure or a single, monolithic structure.

In an embodiment where the quantitative DIC device 100 includes an OFM wavefront sensor, the body is a multi-layer structure. The body forms or includes a fluid channel having a first surface. The body also includes an opaque or semi-opaque aperture layer that is an inner surface layer of the fluid channel. The opaque or semi-opaque aperture layer has light transmissive regions 222 in it. The opaque or semi-opaque aperture layer can be a thin metallic layer in some cases. The body may optionally include a transparent protective layer (not shown) that covers the opaque or semi-opaque aperture layer to isolate the opaque or semi-opaque aperture layer from the fluid and the object 30 moving through the fluid channel.

In general, imaging can be done in many ways. For example, object scanning can be replaced by wavefront sensor scanning by the raster scanning device. As another example, the two-dimensional raster scanning can be replaced by one-dimensional (1D) optofluidic microscope (OFM) scanning scheme described in U.S. patent application Ser. Nos. 11/686,095, 11/743,581, 12/638,518, which are hereby incorporated by reference in their entirety for all purposes. An embodiment of a quantitative DIC device that uses a one dimensional OFM scanning scheme is also described in detail in sections below.

The quantitative DIC devices of embodiments of the invention can be implemented in various ways. In one embodiment, a quantitative DIC device can be in the form of a wavefront sensing chip for use with a microscope, camera or other imaging device. The wavefront sensing chip can be communicatively coupled to the imaging device through a port in the imaging device or the chip can be placed in a housing of the imaging device that accepts the chip. By coupling the wavefront sensing chip to the imaging device, the device can be provided with quantitative DIC functionality such as the ability to capture phase gradient images and compute depth sectioning. For example, a quantitative DIC device can be utilized as a wavefront sensing component of an adaptive optics device. The adaptive optics device operates by measuring distortions in the wavefront and compensating for them with a spatial phase modulator such as a deformable mirror or liquid crystal array.

II. Wavefront Sensor Types

Wavefront sensors of embodiments of the invention can be used in various wavefront sensing applications including adaptive optics, optical testing, adaptive microscopy, retina imaging, etc. An example of using wavefront sensors in adaptive microscopy can be found in Booth, M. J., Neil, M. A. A., Juskaitis, R. Wilson, T, Proceedings of the National Academy of Sciences of the United States of America 99, 5788 (April, 2002), which is herein incorporated by reference in its entirety for all purposes. An example of using wavefront sensors in retinal imaging can be found in Liang, J. Z, Williams, D. R., Miller, D. T., Journal of the Optical Society of America a-Optics Image Science and Vision 14, 2884 (November, 1997), which is herein incorporated by reference in its entirety for all purposes.

The wavefront sensor, which can measure the local intensity and slope of the wavefront modulated by the object (sample) at the same time, can be implemented in several different ways. Three types of wavefront sensors are described below. The first type uses a structured aperture interference (SAI) scheme. The second type uses a Shack-Hartmann scheme. The third type uses the optofluidic microscope (OFM) scheme. These types of wavefront sensors can be used in either a single sensor element (pixel) configuration or in a wavefront sensor array (one or two dimensions) of sensor elements. If a single pixel wavefront sensor is used, a raster scanning device can be used to scan the object or the wavefront sensor to measure two-dimensional image data. If a two-dimensional array of wavefront sensors is used, the array can capture the two-dimensional image in a single snapshot reading. Although three types of wavefront sensors are described below, any suitable type of wavefront sensor can be used in embodiments of quantitative DIC devices.

Wavefront sensors of embodiments can be implemented in conjunction with an imaging system (e.g., a camera system, microscope system, etc.) to provide capabilities such as computing depth sectioning of an object. In these implementations, one or more wavefront sensors can be coupled to the imaging device (e.g., a microscope or camera) or inserted within an imaging device to provide the additional capabilities.

A. Structured Aperture Interference (SAI) Wavefront Sensor

The basic concept of the SAI wavefront sensor is similar to the Young's double-slit phase decoding scheme described in U.S. patent application Ser. Nos. 11/743,581, 11/686,095, and 12/638,518 which is hereby incorporated by reference in its entirety for all purposes. Generally, the local slope of the image wavefront can be measured by looking at the offset of the zero diffraction order on the back detector array (light detector) and the local intensity (amplitude) of the image wavefront can be measured by integrating the diffraction signal on the back detector array.

Figure 6:
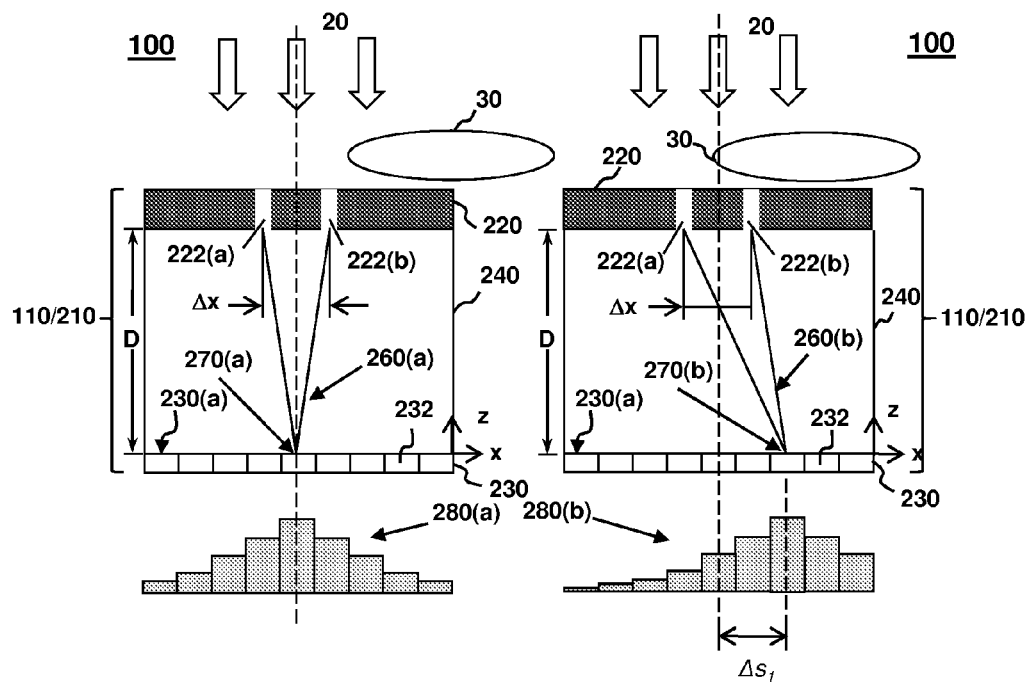
FIG. 6($a$) is a schematic drawing of a side view of components of a quantitative DIC device having a SAI wavefront sensor, according to an embodiment of the invention.

FIGS. 6(a), 6(b) and 6(c) are schematic drawings of a side view of components of a quantitative DIC device 100 having a SAI wavefront sensor, according to embodiments of the invention. The SAI wavefront sensor can be a single pixel wavefront sensor 110 or a wavefront sensor array 210 of one or two dimensions. In the illustrated examples, the SAI wavefront sensor 110/210 is a single pixel wavefront sensor 110 or can be a component of a wavefront sensor array 210 of one or two dimensions.

The SAI wavefront sensor 110/210 comprises an aperture layer 220 (e.g., a metal film), a light detector 230 and a transparent layer 240 between the aperture layer 220 and the light detector 230. The aperture layer 230 includes a first light transmissive region 222(a) and a second light transmissive region 222(b). The two light transmissive regions 222(a) and 222(b) are located at a distance D away from the light detector 230 and are separated from each other by a spacing $\Delta x$. The transparent layer 240 between the light detector 230 and the aperture layer 220 can include one or more layers of transparent material such as water or a viscous polymer (e.g., SU-8 resin), or can be a vacuum or gas-filled space. An illumination source 20 provides illumination (light) to an object 30 which modulates or otherwise alters the light inducing an image wavefront. The light detector 230 measures the distribution of light received from the light transmissive regions 222(a) and 222(b).

A light detector 230 (e.g., photosensor) can refer to any suitable device capable of detecting light and generating signals with wavefront data about the intensity, wavelength, wavefront slope, phase gradient in one or more orthogonal directions, and/or other information about the light being detected. The signals may be in the form of electrical current that results from the photoelectric effect. Some examples of suitable light detectors 230 include a charge coupled device (CCD) or a linear or two-dimensional array of photodiodes (e.g., avalanche photodiodes (APDs)). A light detector 230 could also be a complementary metal-oxide-semiconductor (CMOS) or photomultiplier tubes (PMTs). Other suitable light detectors 230 are commercially available.

The light detector 230 comprises one or more light detecting elements 232. The light detecting elements 232 can be of any suitable size (e.g., 1-4 microns) and any suitable shape (e.g., circular or square). The light detecting elements 232 can be arranged in any suitable form such as a one-dimensional array, a two-dimensional array, and a multiplicity of one-dimensional and/or two-dimensional arrays. The arrays can have any suitable orientation or combination of orientations.

In some cases, the light detecting elements 232 can be arranged in the same form as the light transmissive regions 222(a) and 222(b) and correspond to the light transmissive regions 222(a) and 222(b). The light detector 230 also comprises a first surface 230(a).

In FIGS. 6(a) and 6(b), the object 30 being imaged is homogenous. In FIG. 6(c), the object 30 includes a feature 250 having a refractive index variation from other homogenous portions of the object 30. As an example, the object 30 in FIG. 6(c) could be a cell and the feature 250 may be a nucleus having a different refractive index than other portions of the cell.

In FIGS. 6(a), 6(b) and 6(c), light transmissive region 222(a) collects a reference beam of light and light transmissive region 222(b) collects a sample beam of light. In these examples, the transparent layer (spacer) 240 has a refractive index of n and a thickness of D. When a vertical plane wave is incident on the two light transmissive regions 222(a) and 222(b) of the aperture layer 220, the interference pattern 280 will be centered on the light detector 230. In FIG. 6(a), the vertical plane wave is incident on the two light transmissive regions 222(a) and 222(b) of the aperture layer 220 and the interference pattern 280(a) is centered or substantially centered on the light detector 230. In this illustrated example, the sample beam and reference beams with the same phase exit the two light transmissive regions 222(a) and 222(b), the centroid 270(a) of the light intensity distribution 280(a) of their Young's interference 260(a) is centered or substantially centered on the light detector 230.

If an object 30 is introduced, the phase difference induced by the object 30 between the light transmissive regions 222(a) and 222(b) will shift the centroid 270 of the interference pattern 280 to one side. The phase difference $\Delta\varphi$ is directly related to the offset $\Delta s$ of the interference pattern:

$$\Delta\varphi \approx \frac{2\pi}{\lambda} n \frac{\Delta s}{D} \Delta x, \quad (4)$$

when $\Delta s \ll D$. In addition, the differential phase $$\left(\frac{\partial\varphi}{\partial x}\right)$$

(phase gradient) induced by the object 30 is directly related to the offset ($\Delta s$) of the interference pattern:

$$\frac{\partial\varphi}{\partial x} \approx \frac{2\pi}{\lambda} n \frac{\Delta s}{D}. \quad (5)$$

In FIGS. 6(b) and 6(c), the reference and sample beams carry different phases. In FIG. 6(b), the sample beam passes through a homogeneous portion of the object 30. In this case, the centroid 270(b) of the light intensity distribution 280(b) of their Young's interference 260(b) shifts on the light detector 230 by an offset $\Delta s_1$. In FIG. 6(c), the sample beam passes through a heterogeneous portion of the object 30 and the reference beam passes through a homogenous portion of the object 30. In this case, the centroid 270(c) of the light intensity distribution 280(c) of their Young's interference 260(c) shifts on the light detector 230 by an offset $\Delta s_2$. In some embodiments, the $\Delta s_2$ may be greater than $\Delta s_1$. In other embodiments, the $\Delta s_2$ may be smaller than $\Delta s_1$.

Using Eqns. 4 and 5, the quantitative DIC device 100 can measure the phase difference and the phase gradient of the image wavefront using the measured offset. In addition, the quantitative DIC device 100 can measure the local amplitude by integrating the intensity distribution measured by the light detector 230. By measuring the intensity and phase gradient of the light modulated by the object 30 through independent aspects of the interference pattern, the quantitative DIC device 100 can separate the amplitude and phase information.

The one-dimensional Young's experiment with two slits can be generalized to two dimensions by utilizing varieties of two-dimensional structured apertures e.g., four holes, rose-shaped, ring or Fresnel zone plate, or a single hole. A two-dimensional structured aperture can refer to one or more light transmissive regions 222 in the aperture layer of a wavefront sensor 110/210 where the light transmissive regions extend in two orthogonal directions (e.g., in the x- and y-directions). With two-dimensional structured apertures, the SAI wavefront sensor 110/210 can measure the local slope and phase gradient of the image wavefront in two orthogonal directions (e.g., x-direction and y-direction) at the same time. This aperture-based phase decoding scheme can be referred to as SAI wavefront sensing.

Some embodiments of quantitative DIC devices 100 have an SAI wavefront sensor 110/210 that employs one or more two-dimensional structured apertures to measure the amplitude and differential phase gradient in two orthogonal directions at the same time. In these embodiments, the light transmissive regions of the two-dimensional structure aperture are separated by a thickness D from the light detector. The SAI wavefront sensor 110/210 is generally located at the image plane of the imaging system. The structure aperture selectively transmits and combines the light fields from two directions on the image to create an interference pattern on the light sensor. The total transmission of the interference pattern is proportional to the average image intensity at the light transmissive region.

Generally, wavefront sensors 110/210 (e.g., four holes or single hole aperture sensors) of some embodiments can measure the spatial phase gradient of the light field. Mathematically, the wavefront sensors 110/210 of some embodiments measure:

$$G_x(x,y)=k_x(x,y)/k_0 \approx (d\varphi(x,y)/dx)/k_0, \quad (6)$$

$$G_y(x,y)=k_y(x,y)/k_0 \approx (d\varphi(x,y)/dy)/k_0, \text{and} \quad (7)$$

$$A(x,y), \quad (8)$$

where $G_x(x, y)$ is the two-dimensional phase gradient in the x-direction, $G_y(x, y)$ is the two-dimensional phase gradient in the y-direction, and $A(x, y)$ is the two-dimensional amplitude of the detected wavefront. As such, a quantitative DIC device 100 with a wavefront sensor 110/210 can mathematically reconstruct (unwrap) the detected wavefront by combining the measured data appropriately. One unwrapping method is given by Eq. (9):

$$\psi_{measured}(x, y, z) = A_{measured}(x, y, z)\exp\left(ik_0\left(\int_0^x G_x((x, y=0)dx + \int_0^y G_y(x=x, y)dy\right)\right). \quad (9)$$

Numerous approaches for reconstructing a field distribution exist (unwrapping). The unwrapping methods should all return the same answer if the signal to noise ratio (SNR) of the measurements approaches infinity. The unwrapping methods vary in their performance based on the quantity and type of noise present in the measurements.

Embodiments of the SAI wavefront sensor 110/210 can use any suitable type of two-dimensional structured aperture. For example, the quantitative DIC device 100 can use a two-dimensional structured aperture in the form of a 'plus' sign configuration with four light transmissive regions (e.g., holes) arranged in orthogonal x and y directions. An exemplary quantitative DIC device that uses a four hole structured aperture for differential phase imaging can be found in Lew, Matthew, Cui, Xiquan, Heng, Xin, Yang, Changhuei, *Interference of a four-hole aperture for on-chip quantitative two-dimensional differential phase imaging*, Optic Letters, Vol. 32, No. 20, 2963 (2007), which is hereby incorporated by reference in its entirety for all purposes. Some other examples of two-dimensional structured apertures include a single pedal-shaped aperture, a ring or Fresnel zone plate, and other suitable arrangements of light transmissive regions extending in orthogonal directions.

In some embodiments, a quantitative DIC device 100 has a SAI wavefront sensor 110/210 that employs a two-dimensional structured aperture of four light transmissive regions (e.g., holes) in the form of a 'plus' sign to measure the differential phase and amplitude of an image wavefront in the x-direction and y-direction at the same time. The two long axes of the 'plus' sign are in the orthogonal x and y directions respectively. By placing the SAI wavefront sensor in the image plane of an imaging system, the four transmissive regions will selectively transmit and combine light fields from four adjacent points on the image to create an interference pattern read by the light detector. The total transmission of the interference is proportional to the average image intensity at the light transmissive region. In addition to the spacer thickness D, the offsets $\text{offset}_x(x, y)$ and $\text{offset}_y(x, y)$ of the zero-order interference spot are related to the net wavefront gradient $G_x(x, y)$ and $G_y(x, y)$ at the light transmissive region respectively:

$$G_x(x, y) = \frac{1}{\sqrt{1 + \left(\frac{D}{\text{offset}_x(x, y)}\right)^2}}, \quad (10)$$

$$G_y(x, y) = \frac{1}{\sqrt{1 + \left(\frac{D}{\text{offset}_y(x, y)}\right)^2}}.$$

Figure 7:
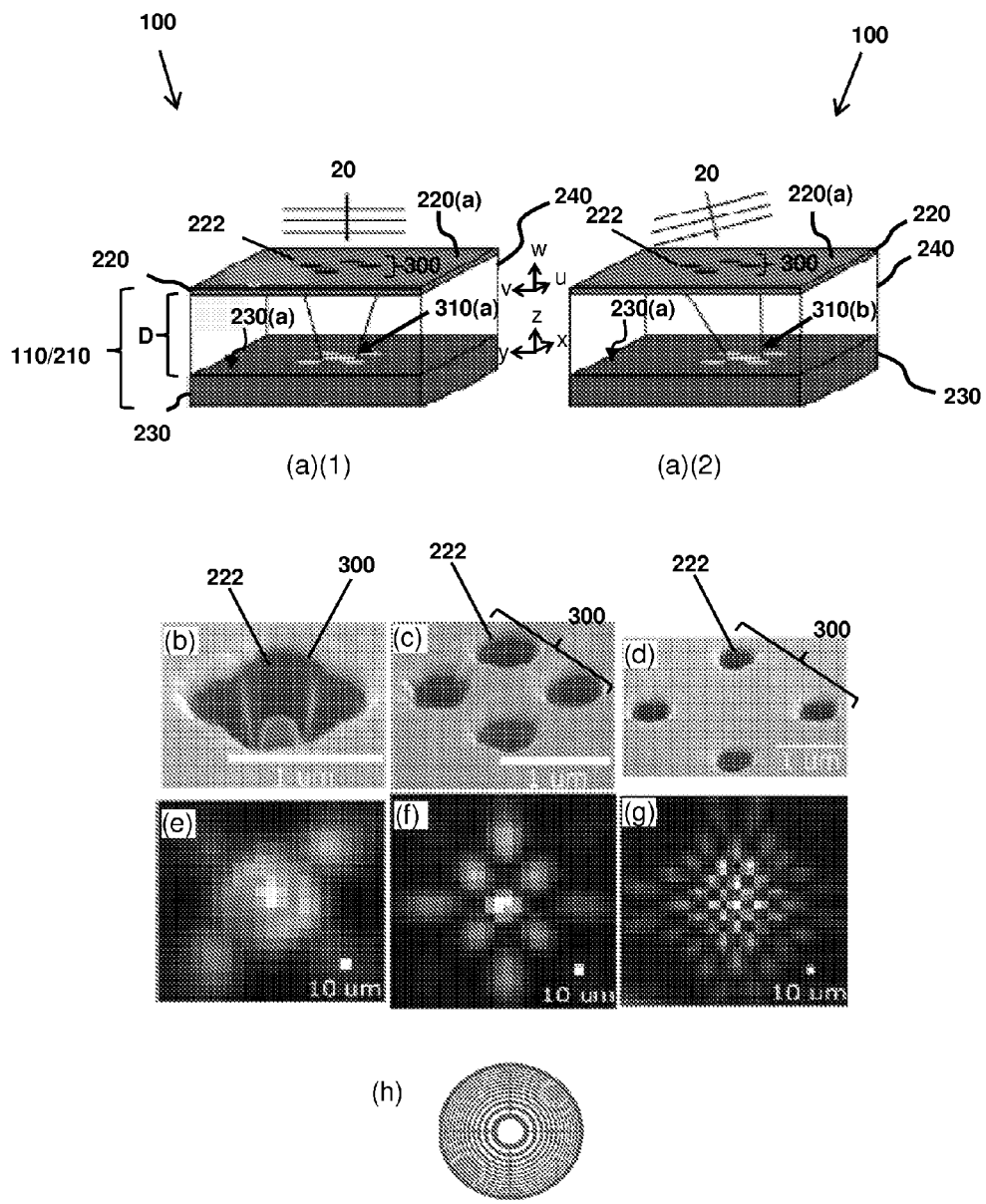
FIG. 7($a$)(1) is a schematic drawing of a perspective view of a two-dimensional structured aperture in the form of a 'plus' sign configuration, according to an embodiment of the invention.

FIGS. 7(a)(1) and 7(a)(2) are schematic drawings of a perspective view of a two-dimensional structured aperture 300 in the form of a 'plus' sign configuration, according to embodiments of the invention. In the illustrated examples, the quantitative DIC device 100 comprises an aperture layer 220 having a two-dimensional structured aperture 300 of four light transmissive regions 222 extending in both x and y directions in a 'plus' sign configuration. Using the two-dimensional structured aperture 300, the quantitative DIC device 100 can measure the differential phase and amplitude in both x and y directions. The quantitative DIC device 100 also has a light detector 230 located at a distance D from the aperture layer 230. The quantitative DIC device 100 also includes a transparent layer 240 with a thickness D located between the aperture layer 220 and the light detector 230. The transparent layer 240 can be comprised of one or more layers of transparent material such as water or a viscous polymer (e.g., SU-8 resin) or can be a vacuum or gas-filled space. Any suitable spacing Δx between the light transmissive regions 222 in the 'plus' sign configuration can be used. Some examples of suitable spacing Δx are 1 μm, 2 μm, or 3 μm.

In FIGS. 7(a)(1) and 7(a)(2), the light detector 230 receives light passing through light transmissive regions 222 in two-dimensional structured aperture 300. In FIG. 7(a)(1), the illumination source 20 projects a light field perpendicular to the first surface 220(a). In FIG. 7(a)(2), the illumination source 20 projects a light field at an angle with respect to the first surface 22(a). The light field projected at different angles in FIG. 7(a)(1) and FIG. 7(a)(2) results in different projections 310(a) and 310(b) respectively onto the light detector 230.

FIGS. 7(b), 7(c), and 7(d) are images taken by a scanning electron microscope of two-dimensional structured apertures 300, according to embodiments of the invention. FIG. 7(b) illustrates a two-dimensional structured aperture 300 in the form of a single pedal-shaped aperture. FIG. 7(c) and FIG. 7(d) illustrate two-dimensional structured apertures 300 of light transmissive regions 222 in the form of a 'plus' sign configuration. The spacing between the light transmissive regions 222 in the structured aperture 300 in FIG. 7(c) is shorter than the spacing between the light transmissive regions 222 in the structured aperture 300 shown in FIG. 7(d). FIGS. 7(e), 7(f), and 7(g) are images of the resulting interference patterns of the two-dimensional structured apertures 300 respectively from FIGS. 7(b), 7(c), and 7(d), according to embodiments of the invention. FIG. 7(h) is a schematic drawing of a Fresnel-zone plate structured aperture with a circular frame.

Figure 8:
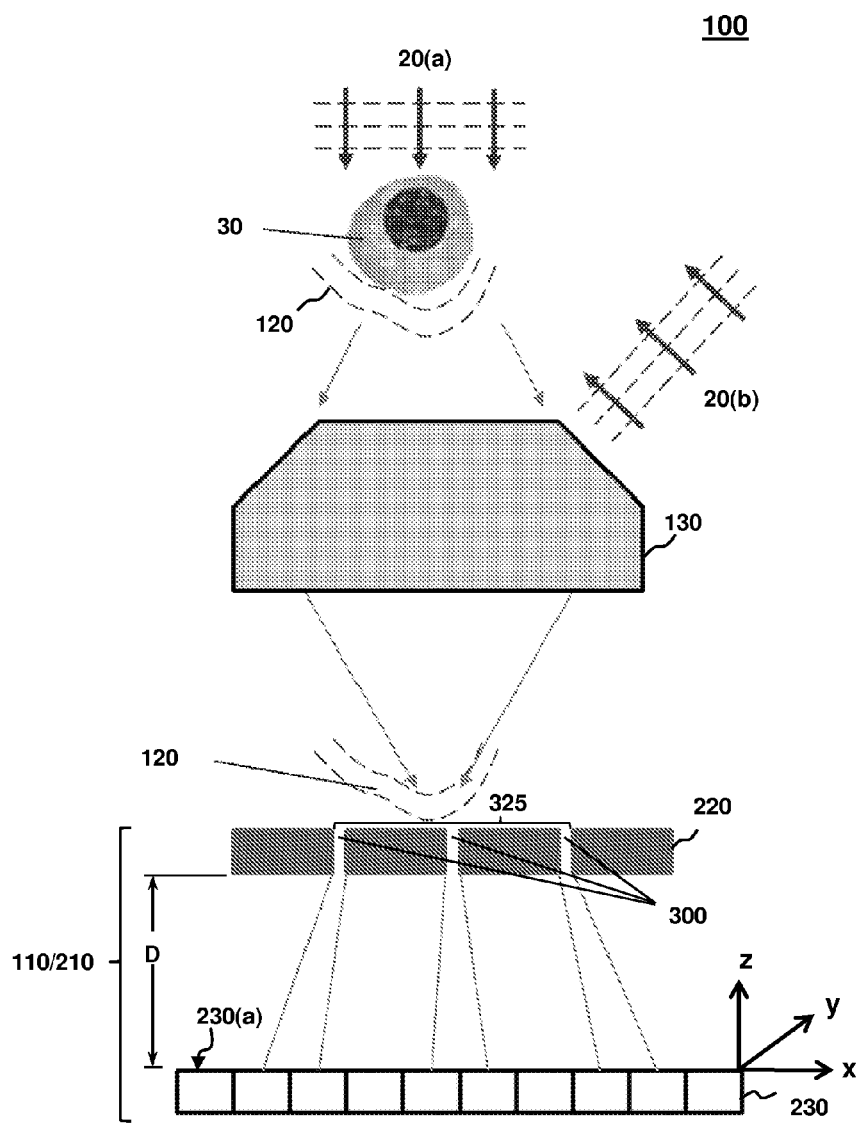
FIG. 8 is a schematic drawing of a side view of components of a quantitative DIC device having a SAI wavefront sensor, in accordance with embodiments of the invention.

FIG. 8 is a schematic drawing of a side view of components of a quantitative DIC device 100 having a SAI wavefront sensor 110/210, in accordance with embodiments of the invention. The SAI wavefront sensor 110/210 has an aperture layer 220 having an array 325 of three structured apertures 300. The SAI wavefront sensor 110/210 also includes a light detector 230 and a transparent layer 240 with a thickness, D located between the aperture layer 220 and the light detector 230. The transparent layer 240 can be comprised of one or more layers of transparent material such as water or a viscous polymer (e.g., SU-8 resin) or can be a vacuum or gas-filled space.

In the illustrated embodiment, the quantitative DIC device 100 is a component of a camera system with a first illumination source 20(a) providing light in the z-direction and a second illumination source 20(b) (e.g., a flash) providing light from another direction. In this example, the light from the additional illumination source reflects off the object 30. The object 30 modulates or otherwise alters the light from both illumination sources 20(a) and 20(b) inducing an image wavefront 120. In other embodiments, the second illumination source 20(b) may be eliminated such as a quantitative DIC device 100 that is a component of a microscope system. In yet other embodiments, other illumination sources may provide light from other directions.

The quantitative DIC device 100 also includes a wavefront relay system 130 (e.g., one or more lenses) in communication with the wavefront sensor 110/120. The wavefront relay system 130 relays the wavefront 120 induced by the object 30 to the SAI wavefront sensor 110/120. In other embodiments, the quantitative DIC device 100 can also include a host computer 150 having a processor 152 and a computer readable medium 154.

In operation, the illumination sources 20(a) and 20(b) provide light to the object 30 inducing the image wavefront 120. The wavefront relay system 130 relays the image wavefront 120 to the structured apertures 300 of the SAI wavefront sensor 110/210. The light passes through the structured apertures. The SAI wavefront sensor 110/210 measures the offsets in the x and y directions of the zero diffraction order of the light distribution read by the light detector 230. The SAI wavefront sensor 110/210 measures the two dimensional phase gradient in the x and y directions based on the offsets using Eqns. (2) and (3). The SAI wavefront sensor 110/210 also measures the amplitude of the image wavefront by integrating the intensity readings over the light detector 230. The quantitative DIC device 100 can then reconstruct the image wavefront 120 using an unwrapping method. The quantitative DIC device 100 can also propagate the reconstructed wavefront to one or more parallel planes intersecting the object 30 in order to compute depth sectioning of the object 30. The quantitative DIC device 100 can also compile the two-dimensional information about the reconstructed and propagated wavefronts to generate three-dimensional information about the object 30. The quantitative DIC device 100 can generate two or three-dimensional images of the object 30 based on the amplitude, phase gradient in a first direction, and/or phase gradient in a second direction orthogonal to the first direction.

The quantitative DIC device 100 also includes an x-axis, a y-axis, and a z-axis. The x-axis and the y-axis lie in the plane of the surface 230(*a*) of the light detector 230. The z-axis is orthogonal to the plane of the surface 230(*a*).

B. Shack-Hartmann Wavefront Sensor

The Shack-Hartmann wavefront sensor includes a microlens array of the same focal length. Each Shack-Hartmann wavefront sensor focuses the local wavefront across each microlens and forms a focal spot onto a photosensor array. The local slope of the wavefront can then be calculated from the position of the focal spot on the light sensor. The principles of the Shack-Hartmann sensors are further described in Platt, Ben C. and Shack, Roland, History and Principles of Shack-Hartmann Wavefront Sensing, Journal of Refractive Surgery 17, S573-S577 (September/October 2001) and in Wikipedia, Shack-Hartmann, at http://en.wikipedia.org/wiki/Shack-Hartmann (last visited Jan. 21, 2009), which are which are hereby incorporated by reference in their entirety for all purposes.

Microlenses can refer to small lenses, generally with diameters of less than about a millimeter and can be as small as about 10 μm. Microlenses can be of any suitable shape (e.g., circular, hexagonal, etc.). Microlenses can also have any suitable surface configuration. In one example, a microlens is a structure with one plane surface and one spherical convex surface to refract light. In another example, a microlens has two flat and parallel surfaces and the focusing action is obtained by a variation of refractive index across the microlens. In another example, a microlens is a micro-Fresnel lens having a set of concentric curved surfaces which focus light by refraction. In yet another example, a microlens is a binary-optic microlens with grooves having stepped edges.

A microlens array can refer to a one or two-dimensional array of one or more microlenses. A Shack-Hartmann wavefront sensor comprises an aperture layer having a microlens array with one or more microlenses located within the light transmissive regions (e.g., holes) in the aperture layer. The Shack-Hartmann wavefront sensor 110/210 also includes a light detector 230 and a transparent layer 240 with a thickness, D located between the aperture layer 220 and the light detector 230. The transparent layer 240 can be comprised of one or more layers of transparent material such as water or a viscous polymer (e.g., SU-8 resin) or can be a vacuum or gas-filled space.

Figure 9:
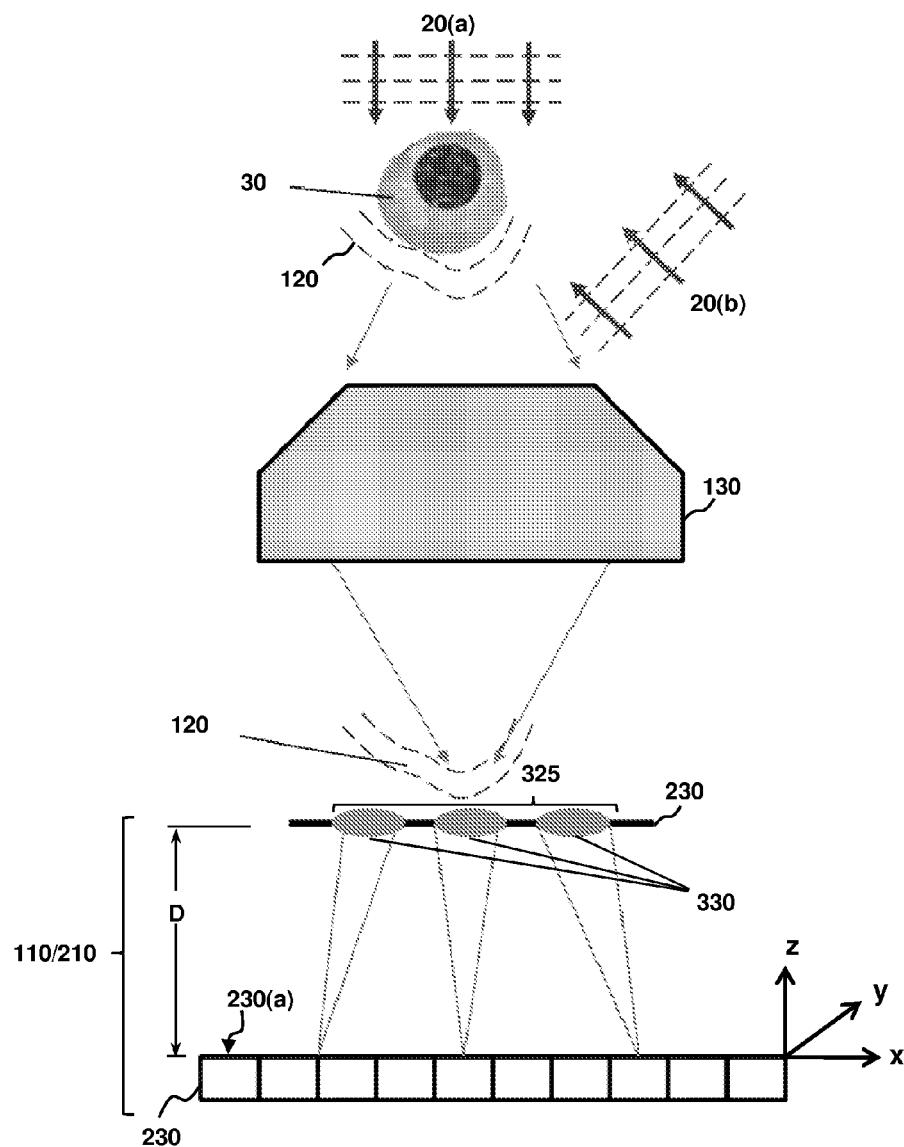
FIG. 9 is a schematic drawing of a side view of components of a quantitative DIC device having a Shack-Hartmann wavefront sensor, in accordance with an embodiment of the invention.

FIG. 9 is a schematic drawing of a side view of components of a quantitative DIC device 100 having a Shack-Hartmann wavefront sensor 110/210, in accordance with an embodiment of the invention. In the illustrated embodiment, the Shack-Hartmann wavefront sensor 110/210 has an aperture layer 230 comprising a microlens array 325 having three microlenses 330.

In the illustrated embodiment, the quantitative DIC device 100 is a component of a camera system with a first illumination source 20(*a*) providing light in the direction of the z-axis and a second illumination source 20(*b*) (e.g., a flash) providing light from another direction. In this example, the light from the additional illumination source reflects off the object 30. The object 30 alters the light from both illumination sources 20(*a*) and 20(*b*) inducing an image wavefront 120. In other embodiments, other illumination sources or a single illumination source may be used. The quantitative DIC device 100 also includes a wavefront relay system 130 (e.g., one or more lenses) in communication with the wavefront sensor 110/120. In other embodiments, the quantitative DIC device 100 can also include a host computer 150 having a processor 152 and a computer readable medium 154.

In operation, the illumination sources 20 provide light to the object 30 inducing the wavefront 120. The wavefront relay system 130 relays the image wavefront 120 induced by the object 30 to the array 320 of microlenses 330. Each microlens 330 concentrates light to focal spots on the light detector 230. The Shack-Hartmann wavefront sensor 110/120 measures offsets of the positions of the focal spots on the light detector 230. The Shack-Hartmann wavefront sensor 110/120 measures the two dimensional phase gradient in x-direction and y-direction and the amplitude as given by Eqns. (2) and (3). The Shack-Hartmann wavefront sensor 110/210 also measures the amplitude of the image wavefront by integrating the intensity readings over the light detector 230. The quantitative DIC device 100 can then reconstruct the image wavefront 120 using an unwrapping method and propagate the wavefront from the plane at the surface 230(*a*) of the light detector 230 to any number of parallel planes intersecting the object 30 to determine image data at different depths through the thickness of the object 30. The quantitative DIC device 100 can also compile the two-dimensional information about the wavefront 120 to generate three-dimensional information about the object 30. The quantitative DIC device 100 can generate two or three-dimensional images of the object 30 based on the amplitude, phase gradient in a first direction, and/or phase gradient in a second direction orthogonal to the first direction.

The quantitative DIC device 100 also includes an x-axis, a y-axis, and a z-axis. The x-axis and the y-axis lie in the plane of the surface 230(*a*) of the light detector 230. The z-axis is orthogonal to the plane of the surface 230(*a*).

C. Optofluidic Microscope (OFM) Wavefront Sensor

The above compact and lensless two-dimensional differential phase measurement scheme can be deployed in OFM imaging scheme as well. By replacing the single light transmissive regions of an intensity OFM device with two-dimensional structured apertures, the intensity OFM device becomes an on-chip and quantitative differential interference contrast optofluidic microscope which can improve image quality while providing high throughput in a compact and inexpensive device. The quantitative DIC device has an OFM wavefront sensor which includes an aperture layer with an array of two-dimensional structured apertures, a light detector, and a transparent layer with a thickness D between the aperture layer and the light detector. The OFM wavefront sensor can determine the amplitude of the image wavefront of an object and determine the phase gradient of the image wavefront in two orthogonal directions of the object. Young's double slit experiment provides a basis for this technique.

Figures 10A, 10B:
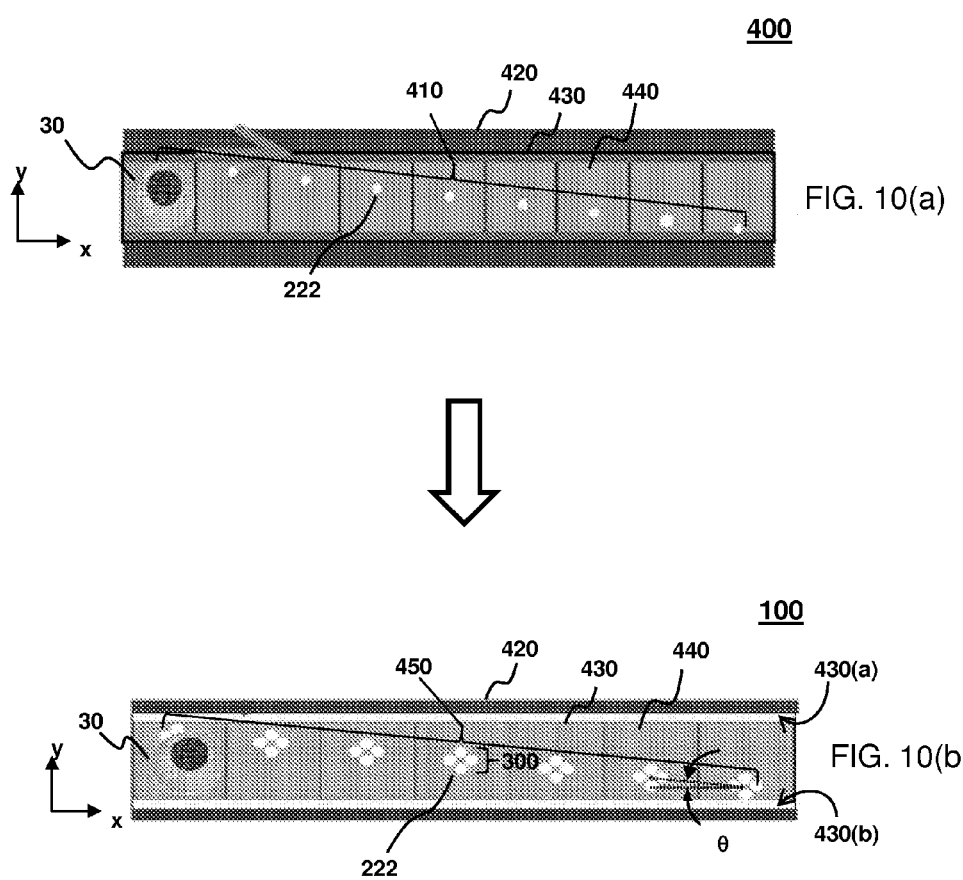
FIG. 10($a$) is a schematic drawing of a top view of components of an intensity OFM device including light transmissive regions in the form of a one-dimensional array of single light transmissive regions.

FIG. 10(a) is a schematic drawing of a top view of components of an intensity OFM device 400 including light transmissive regions 222 in the form of a one-dimensional array 410 of single light transmissive regions 222. The intensity OFM device 400 also includes a body 420 forming or including a fluid channel 430. The light transmissive regions 222 are located in the aperture layer 440 of the body 420. The intensity OFM device 400 also includes a light detector 230 (shown in FIG. 4) having elements for taking time varying readings of the light received through the light transmissive regions 222 as the object 30 travels through the fluid channel 430. The intensity OFM device 400 can use the time varying readings to reconstruct an image of the object 30 based on light intensity detected by the light detector 230.

FIG. 10(b) is a schematic drawing of a top view of components of a quantitative DIC device 100 having an OFM wavefront sensor 210, according to an embodiment of the invention. The quantitative DIC device 100 includes a body 420 comprising an OFM wavefront sensor 210 and forming or including a fluid channel 430. The body 420 can be a multi-layer structure or a single, monolithic structure. In the illustrated example, the body 420 is a multi-layer structure having an opaque or semi-opaque aperture layer 440 that is an inner surface layer of fluid channel 22. The opaque or semi-opaque aperture layer 440 has light transmissive regions 222 in it. The opaque or semi-opaque aperture layer 440 can be a thin metallic layer in some cases. The body 420 may optionally include a transparent protective layer (not shown) that covers the opaque or semi-opaque aperture layer 440 to isolate the opaque or semi-opaque aperture layer 440 from the fluid and the object 30 moving through the fluid channel 430 of the quantitative DIC device 100 having an OFM wavefront sensor 210.

The fluid channel 430 may have any suitable dimensions. For example, the width and/or height of the fluid channel 430 may each be less than about 10, 5, or 1 micron. In some embodiments, the fluid channel 430 may be sized based on the size of the objects 30 being imaged by the quantitative DIC device 100. For example, the height of the fluid channel 430 may be 10 micron where the objects 30 being imaged are 8 micron in order to keep the objects 30 close to the opaque or semi-opaque aperture layer 440, which may help improve the quality of the image. In most embodiments, the flow of the fluid in the fluid channel 430 is generally in the direction of the x-axis.

The OFM wavefront sensor 210 includes a one-dimensional array 450 of structured apertures 300. Each structured aperture 300 is in the configuration of a 'plus' sign configuration of light transmissive regions 222 extending in orthogonal x and y directions. In other embodiments, other configurations (e.g., rose-shaped, ringer shaped, single hole, etc.) can be used. In one embodiment, a microlens is located inside one or more of the light transmissive regions for focusing the light.

The OFM wavefront sensor 210 also includes a light detector 230 (shown in FIG. 8) having elements (e.g., pixels) for taking time varying readings of the light it receives from the light transmissive regions 222 as the object 30 moves through the fluid channel 430. The OFM wavefront sensor 210 also includes a transparent layer (shown in FIG. 8) with a thickness, D between the aperture layer 440 and the light detector 230. The transparent layer 240 can be one or more layers of transparent material such as water or a viscous polymer (e.g., SU-8 resin) or can be a vacuum or gas-filled space. Any suitable spacing $\Delta x$ between the light transmissive regions 222 in the structured apertures 300 can be used. Some examples of suitable spacing $\Delta x$ are 1 μm, 2 μm, or 3 μm.

The quantitative DIC device 100 also includes an illumination source 20 (shown in FIG. 8) to the outside of the opaque or semi-opaque aperture layer 440. Illumination sources such as those shown in FIG. 8 can provide light to the fluid channel 430. As a fluid flows through the fluid channel 430, an object 30 in the fluid is illuminated by the illumination source. The object 30 alters (e.g., blocks, reduces intensity, and/or modifies wavelength) the light passes through, reflecting or refracting off of it to the light transmissive regions 222. The elements in the light detector 230 detect light transmitted through the light transmissive regions 222.

The quantitative DIC device 100 also includes an x-axis and a y-axis that lie in the plane of the inner surface of the light detector 230 proximal to the fluid channel 430. The x-axis lies along a longitudinal axis of the fluid channel 430. The y-axis is orthogonal to the x-axis in the plane of the inner surface of the light detector 230.

The light transmissive regions 222 in the opaque or semi-opaque aperture layer 440 can be of any suitable shape and any suitable dimension. In the illustrated example, the light transmissive regions 222 are holes. The holes may be etched, for example, into the opaque or semi-opaque aperture layer 440 (e.g., a thin metallic layer). In another embodiment, the light transmissive regions 222 may be in the form of one or more slits. A slit can refer to an elongated opening such as a narrow rectangle. Each slit may have any suitable dimension. The slits may have uniform dimensions or may have variable dimensions. The slits can be oriented at any suitable angle or angles with respect to the x-axis of the fluid channel 430.

In the illustrated embodiment, the light transmissive regions 222 in the one-dimensional array 450 of structure apertures 300 collectively extend from one lateral surface 430(a) to another lateral surface 430(b) of the fluid channel 430. The one-dimensional array 450 is located at an angle, $\theta$ with respect to the x-axis. The angle, $\theta$ can be any suitable angle. Although the illustrated embodiment includes a one dimensional array, other embodiments may include an OFM wavefront sensor 210 with other suitable formation(s) of structured apertures 300 can be used such as a slit, a two-dimensional array, or a multiplicity of one-dimensional and/or two-dimensional arrays. In addition, the formations of structured apertures 300 can be in any suitable orientation or combination of orientations.

In operation, the light detector 230 takes time varying readings of the light it receives from the light transmissive regions 222 as the object 30 moves through the fluid channel 430. The quantitative DIC device 100 uses the time varying readings to determine a two dimensional light intensity distribution generated by 'plus' sign configurations of light transmissive regions 222. The quantitative DIC device 100 uses the light intensity distribution to determine the interference in orthogonal directions x and y to determine the offsets. The quantitative DIC device 100 also determines the differential phase (gradient) in orthogonal directions x and y based on the determined interference. The quantitative DIC device 100 also determines the amplitude by summing the intensity of the light detected over an area of the light detector 230 mapping to a particular set of light transmissive regions 222. Examples of methods of measuring the amplitude and differential phase in two orthogonal directions of the sample wavefront quantitatively can be found in Cui, Xiquan, Lew, Matthew, Yang, Changhuei, *Quantitative differential interference contrast microscopy based on structured-aperture interference*, Appl. Phys. Lett. 93, 091113 (2008), which is hereby incorporated by reference in its entirety for all purposes.

In the SAI and OFM wavefront sensors, structured apertures convert the phase gradient of the image wavefront into a measurable form, the offset of the projection of the light field measured by the light detector. In a Shack-Hartmann wavefront sensor, a microlens is used to convert the phase gradient of the image wavefront into a movement of the focal point on the light detector. An advantage of using a SAI or OFM wavefront sensor is that the simple structured apertures provide the ability to build a more compact and cost-effective wavefront sensor than the Shack-Hartmann wavefront sensor having microlenses. In addition, the spacing between the structured apertures in a SAI wavefront sensor can be much shorter than the spacing between the microlenses of the Shack-Hartmann wavefront sensor. Shorter spacing can provide higher spatial resolution and denser wavefront sampling, which can be especially beneficial when detecting complex wavefronts generated by many biological samples.

IV. Computed Depth Sectioning

A. Approach

Computed depth sectioning refers to a technique for determining images at different depths through the thickness of an object 30 using a quantitative DIC device 100 with a wavefront sensor 110/210. Any type of wavefront sensor 110/210 can be used. In some embodiments, polarization effects are ignored. For simplicity, it is assumed that in these embodiments this technique is premised on a light field that is linearly polarized and on no interactions in the light field depolarizing or in any other way disrupting the polarization of the light field.

The approach to the computed depth sectioning technique is primarily based on two concepts. According to a first concept, the light field at any given plane z can be fully described by a complete set of spatially varying amplitude and phase information. In other words, a light field at plane z can be described by Eq. (11) as:

$$\psi(x,y,z) = A(x,y,z)\exp(i\phi(x,y,z)), \quad (11)$$

where $\psi(x, y, z)$ is the light field at plane z, $A(x, y, z)$ is the amplitude at plane z and $\phi(x, y, z)$ is the phase at plane z. A second concept provides the Huygen's principle which states that the light field at an earlier or later (higher or lower z value) plane can be calculated from the light field at plane z. In other words, a known function (f) connects according to Eq. (12):

$$\psi(x,y,z+\Delta z) = f(\psi(x,y,z),\Delta z), \quad (12)$$

where $\psi(x, y, z+\Delta z)$ is the light field at plane $(z+\Delta z)$. The function (f) is well known and studied in electromagnetic theory. For example, this function f is described in Kraus, John Daniel, Fleisch, Daniel A., Electromagnetics with Applications (5th Ed), Chapters 4-16 (1999), which is herein incorporated by reference in its entirety for all purposes. This computation assumes the absence of unknown scattering objects between plane z and plane $(z+\Delta z)$.

These two concepts are powerful when applied to phase imaging in embodiments of the invention. It implies that if one can measure the phase and amplitude distribution at the plane of the sensor (plane z), one can calculate and render the light field distributions at different heights (different $(z+\Delta z)$ planes) above the sensor. The light field distributions are, in effect, images at those chosen planes. According to this treatment, if a wavefront sensor can measure the two dimensional phase and amplitude data at a light detector plane z, the quantitative DIC device can use this data to numerically reconstruct the image and numerically propagate it to any plane $z+\Delta z$ above or below the plane z of the light detector.

The propagation of the light field is governed by Maxwell's equations entirely. If one can measure the phase and amplitude distribution of the light field at the sensor, one can take that information and calculate the light field distribution at any given plane above the sensor (or below the sensor). The amplitude distribution of the computed light field is equivalent to the traditional microscope image taken at the focal plane set at $z+\Delta z$. This treatment is strictly true if no unknown object is present between the plane z and $z+\Delta z$.

Figure 11:
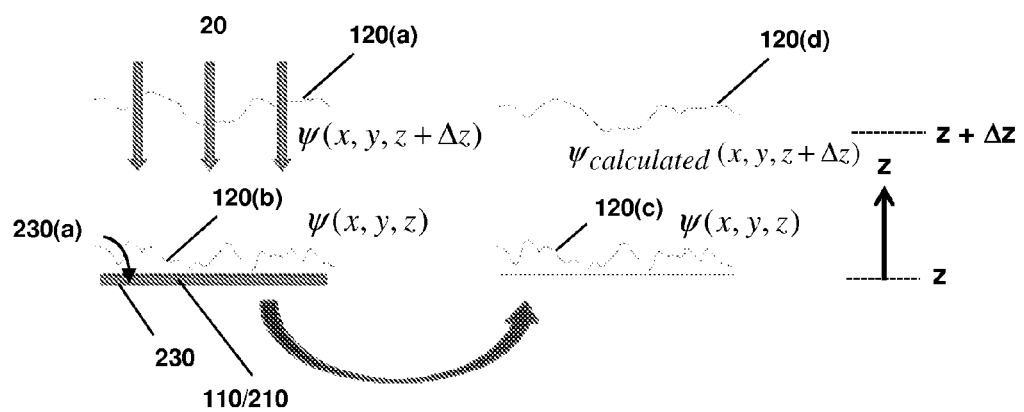
FIG. 11 illustrates a schematic diagram illustrating this propagation approach, according to embodiments of the invention.

FIG. 11 illustrates a schematic diagram illustrating this propagation approach, according to embodiments of the invention. In the illustrated example, an illumination source 20 provides light. The light distribution of a first wavefront 120(a) is $\psi(x, y, z+\Delta z)$ at plane $z+\Delta z$. In this example, plane z refers to a plane perpendicular to the z-axis and coinciding with the surface 230(a) of the light detector 230 of wavefront sensor 110/210. Plane $z+\Delta z$ refers to a plane parallel to plane z and at a distance $\Delta z$ from plane z.

In FIG. 11, the light detector 230 of the wavefront sensor 110/210 measures the light distribution $\psi(x, y, z)$ of the second (detected) wavefront 120(b) at plane z. The light detector 230 measures the two-dimensional amplitude and two-dimensional phase gradient data in two orthogonal directions, associated with the second (detected) wavefront 120(b) at plane z based on the measured light distribution $\psi(x, y, z)$. A processor 152 of the wavefront sensor 110/210 or of the host computer 150 numerically reconstructs a third (reconstructed) wavefront 120(c) having the light distribution $\psi(x, y, z)$ using the measured phase and amplitude information of the detected wavefront 120(b). The processor 152 of the wavefront sensor 110/210 or of the host computer 150 calculates and renders a light distribution $\psi_{calculated}(x, y, z+\Delta z)$ of a fourth (propagated) wavefront 120(d) at a plane $z+\Delta z$ based on the reconstructed light distribution $\psi(x, y, z)$. That is, the processor 152 of the wavefront sensor 110/210 or of the host computer 150 numerically propagates the reconstructed wavefront 120(c) from plane z to the plane $z+\Delta z$ to generate the fourth (propagated) wavefront 120(d).

The imaging of an unknown but weak scatterer (e.g., a transparent object) can be performed computationally using the same mathematical frame work as described above—by ignoring the presence of the scatterer during the calculation and back-computing the light field at $z+\Delta z$. Using this frame work by ignoring the presence of the object, the quantitative DIC device can image an object by computationally back propagating a reconstructed image of the object at plane z to parallel planes above and below the plane z.

Figure 12:
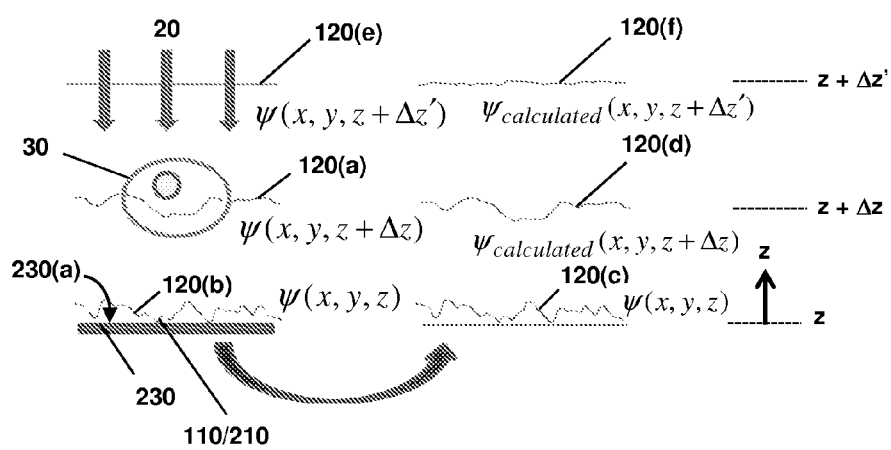
FIG. 12 is a schematic diagram of the propagation approach using a processor, according to embodiments of the invention.

FIG. 12 is a schematic diagram of the propagation approach using a processor, according to embodiments of the invention. In this example, the illumination source generates a uniform wavefront 120(e) associated with a uniform light distribution of $\psi(x, y, z+\Delta z')$ at plane $z+\Delta z'$. Plane $z+\Delta z'$ refers to a plane between the illumination source 20 and the object 30, that is parallel to plane z, and that is at a distance $\Delta z'$ from plane z. At plane $z+\Delta z$, the object 30 induces a first (induced) wavefront 120(a) associated with a light distribution of $\psi(x, y, z+\Delta z)$. Plane $z+\Delta z$ refers to a plane parallel to plane z and at a distance $\Delta z$ from plane z. The light detector 230 of the wavefront sensor 110/210 measures the light distribution $\psi(x, y, z)$ of the second (detected) image wavefront 120(b) at plane z. The light detector 230 measures the amplitude and phase gradient of the second (detected) image wavefront 120(b) at plane z based on the light distribution $\psi(x, y, z)$. In this example, plane z refers to a plane perpendicular to the z-axis and coinciding with the surface 230(a) of the light detector 230 of wavefront sensor 110/210.

A processor 152 of the wavefront sensor 110/210 or of the host computer 150 numerically reconstructs the light distribution $\psi(x, y, z)$ of a third (reconstructed) image wavefront 120(c) based on the measured phase and amplitude information of the detected image wavefront 120(b). The processor 152 of the wavefront sensor 110/210 or of the host computer 150 calculates and renders a computed light distribution $\psi_{calculated}(x, y, z+\Delta z)$ of a first (propagated) image wavefront 120(d) at a plane $z+\Delta z$ based on the reconstructed light distribution $\psi(x, y, z)$. That is, the processor 152 of the wavefront sensor 110/210 or of the host computer 150 numerically propagates the reconstructed image wavefront 120(c) from plane z to the plane $z+\Delta z$ to generate a first propagated image wavefront 120(d) that approximates the first induced wavefront 120(a). The processor 152 of the wavefront sensor 110/210 or of the host computer 150 also calculates and renders a computed light distribution $\psi_{calculated}(x, y, z+\Delta z')$ of a second propagated image wavefront 120(f) at a plane $z+\Delta z'$ based on the reconstructed wavefront 120(c) or based on the first propagated image wavefront 120(d). The second propagated image wavefront 120(f) approximates the image wavefront 120(e) associated with the uniform light distribution $\psi(x, y, z+\Delta z)$. In the same way, the processor 152 of the wavefront sensor 110/210 or of the host computer 150 can numerically propagate the reconstructed image wavefront 120(c) or any previously propagated image wavefronts to other z-planes at any height through the thickness of the object 30. The processor 152 of the wavefront sensor 110/210 or of the host computer 150 can compute the depth sectioning of the object 30 by propagating image wavefronts at different heights through the object 30.

The amplitude distribution of the computed light field is equivalent to the traditional microscope image taken at the focal plane set at $z+\Delta z$. In fact, it can be identical. In the traditional microscope, the calculation is performed optically by the optical elements. By adjusting the optics (e.g., lenses), one can bring different planes into focus but effectively what one is doing is making slight adjustments to the optical computing process.

Figures 13A, 13B:
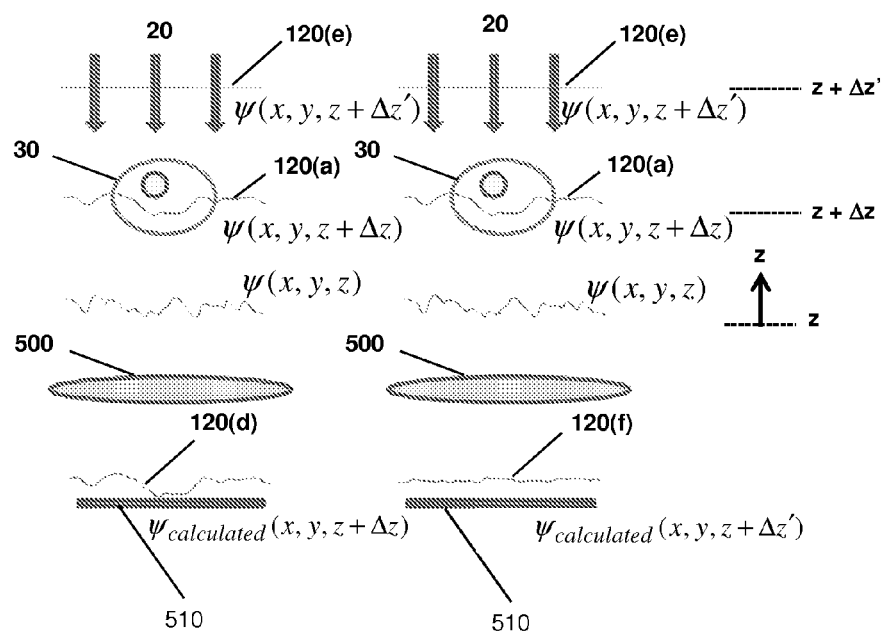
FIGS. 13($a$) and 13($b$) are schematic drawings of a focusing approach taken by a traditional microscope.

FIGS. 13(a) and 13(b) are schematic drawings of a focusing approach taken by a traditional microscope. In this approach, the optical elements (e.g., lenses) are moved to bring different planes into focus. In FIG. 13(a), the microscope is adjusting the optics to bring plane $z+\Delta z$ into focus. In FIG. 13(b), the microscope is adjusting the optics to bring plane $z+\Delta z'$ into focus.

In FIG. 13(a), the illumination source generates a uniform wavefront 120(e) associated with a uniform light distribution of $\psi(x, y, z+\Delta z')$ at plane $z+\Delta z'$. Plane $z+\Delta z'$ refers to a plane between the illumination source 20 and the object 30, that is parallel to plane z, and that is at a distance $\Delta z'$ from plane z. At plane $z+\Delta z$, the object 30 induces a first (induced) wavefront 120(a) associated with a light distribution of $\psi(x, y, z+\Delta z)$. Plane $z+\Delta z$ refers to a plane parallel to plane z and at a distance $\Delta z$ from plane z. The optical elements 500 are placed at a distance away from the sensor 510 to calculate a light distribution of $\psi_{calculated}(x, y, z+\Delta z)$ to focus an image wavefront 120(f) on plane $z+\Delta z$.

In FIG. 13(b), the illumination source generates a uniform wavefront 120(e) associated with a uniform light distribution of $\psi(x, y, z+\Delta z')$ at plane $z+\Delta z'$. Plane $z+\Delta z'$ refers to a plane between the illumination source 20 and the object 30, that is parallel to plane z, and that is at a distance $\Delta z'$ from plane z. At plane $z+\Delta z$, the object 30 induces a first (induced) wavefront 120(a) associated with a light distribution of $\psi(x, y, z+\Delta z)$. Plane $z+\Delta z$ refers to a plane parallel to plane z and at a distance $\Delta z$ from plane z. The optical elements 500 are placed at a distance away from the sensor 510 to calculate a light distribution of $\psi_{calculated}(x, y, z+\Delta z')$ to focus an image wavefront 120(f) on plane $z+\Delta z'$.

In some cases, the process may not be perfect because one may not achieve a good image if the scatterer is thick and/or highly scattering because the assumption that the scatterer is ignorable in the computation process may be violated. However, this problem can affect computation-based depth sectioning using a quantitative DIC device and optical-based sectioning using a traditional microscope equally. The axiom of 'no free lunch' can apply equally in both situations. For thin tissue sections or cell samples, the distortion may be nominally tolerable. In practical situations, one can typically deal with a 100 microns thick tissue sample before distortion starts becoming significant.

A sensor capable of spatially measuring amplitude and phase is required to compute depth sectioning of the object based on the propagation approach. The wavefront sensors embodiments have the capability of measuring the two-dimensional amplitude and phase required to compute depth sectioning of the object. In addition, the signal to noise ratio of the sensor measurements may need to be high in some cases. Otherwise the computed images may be poor in quality.

Modifications, additions, or omissions may be made to the quantitative DIC device 100 of any configuration or to the wavefront sensors 110 or 210 of any type (e.g., SAI wavefront sensor, Shack-Hartman wavefront sensor, and OFM wavefront sensor) without departing from the scope of the disclosure. The components of the quantitative DIC device 100 of any configuration or to the wavefront sensors 110 or 210 of any type may be integrated or separated according to particular needs. For example, the processor 152 may be a component of the light detector 230. Moreover, the operations of the quantitative DIC device 100 may be performed by more, fewer, or other components and the operations of the wavefront sensors 110 or 210 may be performed by more, fewer, or other components. Additionally, operations of the quantitative DIC device 100 or wavefront sensors 110/210 may be performed using any suitable logic comprising software, hardware, other logic, or any suitable combination of the preceding.

B. Flow Chart

Figure 14:
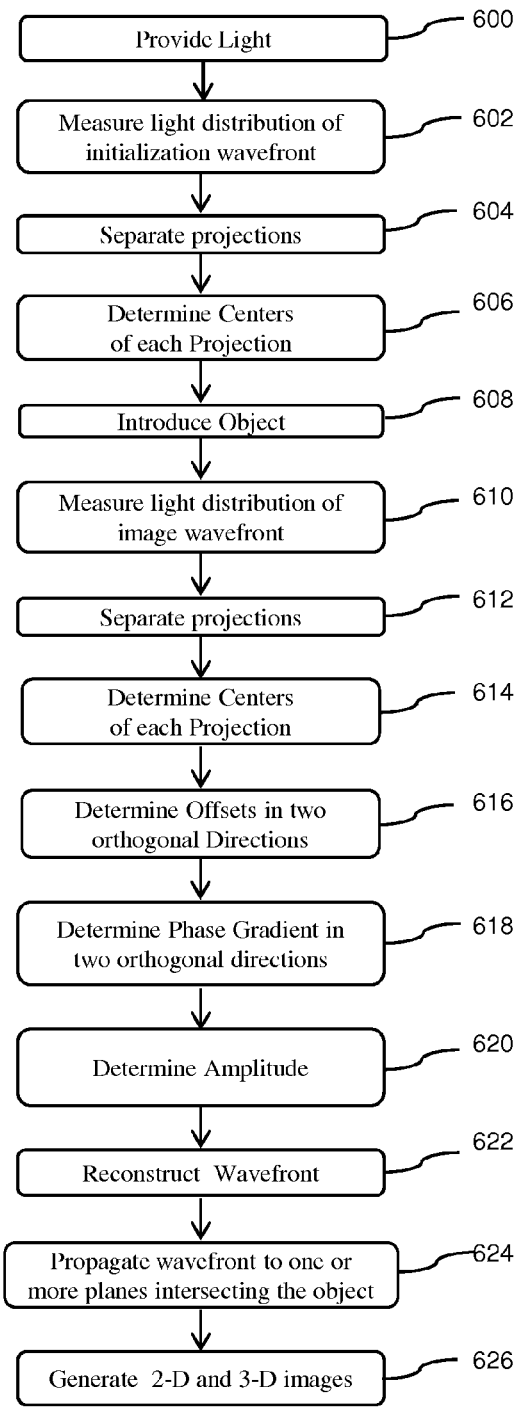
FIG. 14 is a flow chart of a compute depth sectioning method using a quantitative DIC device having a wavefront sensor, according to embodiments of the invention.

FIG. 14 is a flow chart of a compute depth sectioning method using a quantitative DIC device 100 having a wavefront sensor 110/210, according to embodiments of the invention. The quantitative DIC device 100 used in this method can have any suitable type of wavefront sensor 110/210. Suitable types of wavefront sensors 110/210 include a SAI wavefront sensor, Shack-Hartmann wavefront sensor, OFM wavefront sensor, or other suitable wavefront sensor. In addition, any suitable configuration of wavefront sensor wavefront sensor 110/210 can be used. For example, the quantitative DIC device 100 can have a single pixel wavefront sensor 110, a one dimensional array of sensor elements 210, a two-dimensional wavefront sensor array 210, etc. If the wavefront sensor wavefront sensor 110/210 is a single pixel wavefront sensor, a raster scanning device can be employed to scan the wavefront sensor or the object to get a two-dimensional reading at a single time. If the wavefront sensor 110/210 is a two-dimensional wavefront sensor array, the wavefront sensor can take a two-dimensional reading of the image wavefront at the same time. If the wavefront sensor 110/210 is a one-dimensional array, the wavefront sensor 110/210 can read time varying data in the form of line scans and compile the line scans to generate two-dimensional wavefront data.

The method begins with an illumination source or sources 20 providing light (step 600). Without the object 30 being present, the light generates an initialization wavefront with a light distribution of $\psi(x, y, z+\Delta z')$ at plane $z+\Delta z'$ of the illumination source 20. The illumination source or sources 20 can provide light in any suitable direction(s). If the quantitative DIC device 100 is a component of a camera system, multiple illumination sources 20 such as a flash, ambient light, etc. may provide light from multiple directions. If the quantitative DIC device 100 is a component of a microscope, a single illumination source 20 may provide light in a single direction along the z-axis toward the wavefront sensor. In one embodiment, a wavefront relay system 130 relays or projects the wavefront to the wavefront sensor. In other embodiments, the wavefront relay system 130 is eliminated and the wavefront is projected directly to the wavefront sensor 110/210.

Next, the wavefront sensor 110/210 measures the light distribution $\psi(x, y, z)$ of the initialization wavefront 120 at plane z (step 602). The initialization wavefront is received through the structured apertures 300 by the light detecting elements 232 of the light detector 230. If the wavefront sensor is a single pixel wavefront sensor 110, the light detector 230 uses a raster scanning device 140 to scan the wavefront sensor 110/210 or the object 30 to generate a reading of the two dimensional light intensity distribution at a single time. If the wavefront sensor is a two dimensional sensor array, the light detector 230 can read the two dimensional light intensity distribution in a snapshot reading without raster scanning. If the wavefront sensor is a one dimensional sensor array using an OFM scheme (OFM wavefront sensor), the light detector 230 reads time varying data as the object 30 passes through the fluid channel. The time varying data can be in the form of line scans which can be compiled to generate the two dimensional light distribution.

The processor 152 of the wavefront sensor 110/210 or of the host computer 150 separates the light projection/distribution of each structured aperture 300 from the light projection/distribution from other structured apertures 300 (step 604). Once separated, the light distributions/projections can be used to map the light detecting elements 232 of the light detector 230 to the structured apertures 300.

Any suitable technique for separating the projections/distributions can be used. In one embodiment, separation can be performed by suppressing the crosstalk from adjacent projections of the wavefront 120 through adjacent structured apertures 300. In this embodiment, the processor 152 can determine the maximum intensity values of the light distribution. The processor 152 can then determine the light detecting elements 232 that have read the maximum intensity values. The processor 152 can determine the midpoint on the light detector 230 between the light detecting elements 232 reading the maximum intensity values. The processor 152 can then use the midpoint to separate the light detecting elements reading the light distribution from particular structured apertures 300. Alternatively, a predefined number of light detecting elements 232 around each light detecting element 232 with the maximum intensity value can define the light detecting elements 232 associated with each structured aperture 300.

Next, the processor 152 predicts the center of each projection/distribution 300 (step 606). Any method can be used to predict the initial centers. In one embodiment, the processor 152 may determine that the center of each projection/distribution is the light detecting element having the highest intensity value.

The object 30 is introduced (step 608). In other embodiments, steps 602 through 606 can be performed after step 614 and before step 616. The object 30 can be introduced using any suitable technique. For example, the object 30 may be injected with a fluid sample into an input port of the quantitative DIC device 100.

Figure 15A:
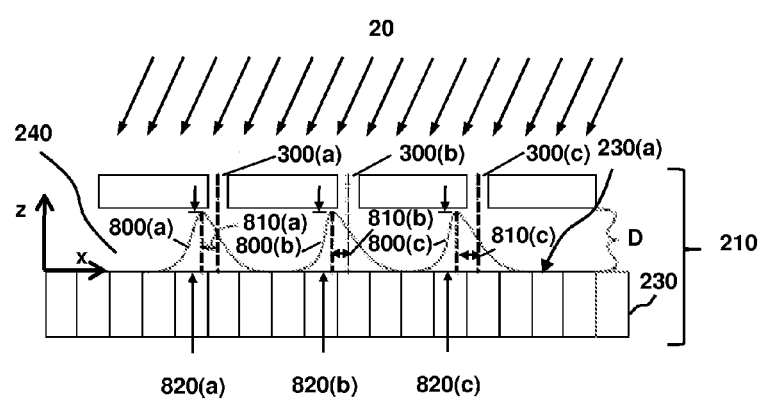
FIG. 15($a$) is a side view of components of the wavefront sensor, according to an embodiment of the invention.
Figure 15B:
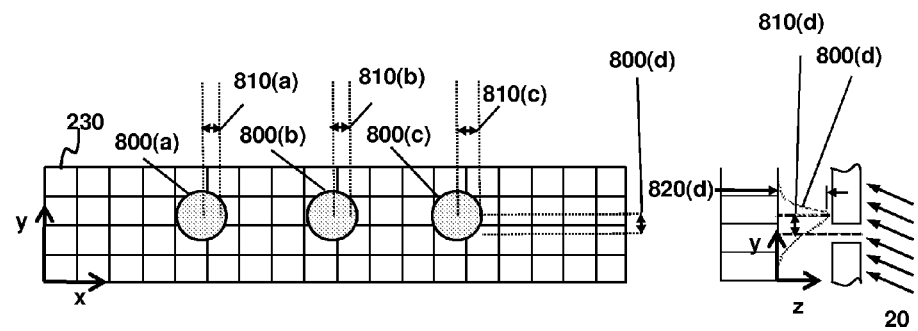
Figure 15C:
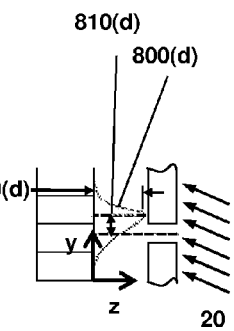

Once introduced, the object 30 alters the light from the illumination source 20 and induces an image wavefront 120 at $z+\Delta z$ having a light distribution $\psi(x, y, z+\Delta z)$. Referring to FIGS. 15(a), 15(b), and 15(c), a wavefront sensor 210 is shown with an image wavefront induced by an object, according to an embodiment of the invention. FIG. 15(a) is a side view of components of the wavefront sensor 210, according to an embodiment of the invention. The wavefront sensor 210 includes an aperture layer 220 having an array of three structured apertures 300(a), 300(b) and 300(c) along the x-axis. FIG. 15(b) is a top view of components of the wavefront sensor 210 in FIG. 15(a), according to an embodiment of the invention. FIG. 15(c) is a sectional view of components of the wavefront sensor 210 in FIG. 15(a) through the center of structured aperture 300(c), according to an embodiment of the invention. Although three structured apertures 300(a), 300(b) and 300(c) are shown, any number of structured apertures can be used. In addition, any type of structured aperture (e.g., four hole, single hole, etc.) may be used.

In FIGS. 15(a), 15(b), and 15(c), the wavefront sensor 210 also includes a light detector 230 having a surface 230(a) and a transparent layer 240 between the light detector 230 and the aperture layer 220. The transparent layer 240 has a thickness D. Although the illustrated example shows the light detector 230 comprising a two-dimensional array of light detecting elements, any suitable number or configuration of light detecting elements 232 can be used. For example, a single light detecting element 232 can be used.

Returning to FIG. 14, the wavefront sensor measures the light distribution $\psi(x, y, z)$ of the wavefront induced by the object 30 (step 610). The wavefront is measured at plane z of the light detector corresponding to surface 230(a) of the light detector 230.

In the illustrated embodiment shown in FIGS. 15(a), 15(b), and 15(c), the wavefront 120 is received through the structured apertures 300(a), 300(b) and 300(c) in the aperture layer 220 by the light detecting elements 232 of the light detector 230. The light detector 230 can take a two-dimensional snapshot reading of the light distribution or can use a raster scanning device 140 to scan the wavefront sensor to get a two-dimensional reading at a single time. In another embodiment, the light detector 230 can read time varying intensity information through structured apertures 300 of an OFM wavefront sensor. In this case, the light distribution is compiled from line scans of the time varying information.

Returning to FIG. 14, the processor 152 of the wavefront sensor or the host computer separates the light distribution/projection (step 612). In the illustrated embodiment shown in FIGS. 15(a), 15(b), and 15(c), the processor 152 separates the light distributions 800(a), 800(b) and 800(c) from a particular light transmissive region 232 of a structured aperture 300 from the light distribution projected from light transmissive regions 232 of other structured apertures 300. For example, the processor 152 separates the light distribution 800(a) associated with structured aperture 300(a) from the light distributions 800(b) and 800(c) associated with the structured apertures 300(b) and 300(c). The separation of the light distributions/projections can be used to map the light detecting elements 232 of the light detector 230 to the light transmissive region(s) of the structured apertures 300.

Any suitable method of separating the projections/distributions 800(a), 800(b) and 800(c) can be used. In one embodiment, separation can be performed by suppressing the crosstalk from adjacent projections of the wavefront 120 through adjacent structured apertures 300(a), 300(b) and 300(c). The processor 152 of the quantitative DIC device 100 determines the maximum intensity values 820(a), 820(b), 820(c), and 820(d) of the light distributions 800(a), 800(b) and 800(c) in both orthogonal x- and y-directions. The processor 152 then determines the light detecting elements 232 reading the maximum intensity values 820(a), 820(b) and 820(c). The processor 152 can determine the midpoint on the light detector 230 between the light detecting elements 232 reading the maximum intensity values 820(a), 820(b), 820(c), and 820(d). The processor 152 can then use the midpoint to separate the light detecting elements reading the light distribution from particular structured apertures 300. Alternatively, a predefined number of light detecting elements 232 around the light detecting element 232 reading the maximum intensity value can define the light detecting elements 232 associated with each structured aperture 300. For example, all light detecting elements 232 within three light detecting elements of the one reading the maximum intensity value can be associated with the light distribution from a particular structured aperture 300.

Returning to FIG. 14, the processor 152 also predicts the center of the projections associated with the structured apertures (step 614). Any method can be used to predict the centers. In one embodiment, the processor 152 may determine that the center of each separated projection/distribution is the light detecting element having the highest intensity value.

Next, the processor 152 determines the x and y offsets (step 616). The processor 152 can determine the offsets from the change in position of the center in both the x and y directions of each projection before and after an object is introduced. In FIGS. 15(a), 15(b), and 15(c), the processor 152 determines the offset 810(a) at structured aperture 300(a) in the x-direction, offset 810(b) at structured aperture 300(b) in the x-direction and offset 810(c) at structured aperture 300(c) in the x-direction. The processor 152 also determines an offset 810(d) at aperture 300(c) in the y-direction. Although not shown, the processor 152 also determines offsets in the y-direction at apertures 300(a) and 300(b). In another embodiment, the processor 152 may determine the offsets from a change in the position of another portion of each projection before and after the object is introduced.

Returning to FIG. 14, the processor 152 determines the phase gradient in two orthogonal directions (step 618). The processor 152 can determine the local phase gradient in two orthogonal directions based on the offsets in the x and y directions using Eqns. (2) and (3). Generally, wavefront sensors having structured apertures 300 (e.g., four hole aperture or single hole aperture sensors) of some embodiments can measure the spatial phase gradient of the light field. Mathematically, the wavefront sensors of some embodiments measure:

$$G_x(x,y)=k_x(x,y)/k_0 \approx (d\phi(x,y)/dx)/k_0, \quad (6)$$

$$G_y(x,y)=k_y(x,y)/k_0 \approx (d\phi(x,y)/dy)/k_0, \text{ and} \quad (7)$$

$$A(x,y), \quad (8)$$

where $G_x(x, y)$ is the two-dimensional phase gradient in the x-direction, $G_y(x, y)$ is the two-dimensional phase gradient in the y-direction, and $A(x, y)$ is the two-dimensional amplitude of the detected wavefront. To determine the phase gradient in two orthogonal directions based on the offsets, the processor 152 can measure the net wavefront gradient $G_x(x, y)$ and $G_y(x, y)$ at each aperture respectively based on Eq. (10):

$$G_x(x, y) = \frac{1}{\sqrt{1+\left(\frac{D}{offset_x(x,y)}\right)^2}} \quad (10)$$

and $$G_y(x, y) = \frac{1}{\sqrt{1+\left(\frac{D}{offset_y(x,y)}\right)^2}},$$

where D is the transparent layer (spacer) thickness, the offset in the x-direction is $offset_x(x,y)$ and the offset in the y-direction is $offset_y(x,y)$.

The processor 152 also measures the amplitude of the image wavefront 120 (step 620). The processor 152 measures the amplitude by summing up all the intensity values in each separated projection/distribution associated with each structured aperture 300. With the amplitude and phase gradient information, the quantitative DIC device 100 has sufficient data to reconstruct the image wavefront at the plane z at the light detector 230.

The quantitative DIC device 100 can mathematically reconstruct (unwrap) the detected wavefront by combining the measured data appropriately using an unwrapping method (step 622). One unwrapping method is given by Eq. (9):

$$\psi_{measured}(x, y, z) = A_{measured}(x, y, z)\exp\left(ik_0\left(\int_0^x G_x((x, y = 0)dx + \int_0^y G_y(x = x, y)dy\right)\right). \quad (9)$$

Numerous approaches for reconstructing a field distribution exist (unwrapping). Some examples of suitable unwrapping methods include the Affine transformation method, the least squares method, the Frankot Chellappa methods of wrapping, etc. The unwrapping methods should all return the same answer if the signal to noise ratio (SNR) of the measurements approaches infinity. The unwrapping methods may vary in their performance based on the quantity and type of noise present in the measurements.

The processor 152 propagates the reconstructed wavefront at plane z to one or more planes z+Δz intersecting the object 30 (step 624). The processor 152 propagates the reconstructed wavefront having a distribution ψ(x, y, z) to the other planes based on Eq. (12): ψ(x, y, z+Δz)=f(ψ(x, y, z), Δz) where ψ(x, y, z+Δz) is the light distribution at plane (z+Δz) intersecting the object 30. The function (f) is well known and studied in electromagnetic theory. For example, this function f is described in Kraus, John Daniel, Fleisch, Daniel A., Electromagnetics with Applications (5th Ed), Chapters 4-16 (1999).

The processor 152 may propagate the reconstructed wavefront to any number of planes (z+Δz) at different depths through the object 30. In one embodiment, the object 30 may have a dimension h along the z axis and may be located adjacent to the surface 230(a) of the light detector 230. The processor 152 may propagate the reconstructed wavefront n times (e.g., 100, 1000, 2000, etc.) through the planes z+Δz$_{k=1\ to\ n}$ where Δz$_k$=Δz$_1$+hk/n. In this case, the reconstructed wavefront is propagated to n depths starting at the surface 230(a) where n=1 and incrementally increasing the depths by hk/n. In other embodiments, particular depths are used to image a region of the object 30. For example, the processor 152 may propagate the reconstructed wavefront to a plane at the middle of the object 30.

The processor 152 generates two-dimensional and three-dimensional images (step 626). In one embodiment, the processor 152 generates two-dimensional images based on the reconstructed wavefront, the intensity distribution, the phase gradient distribution in the x-direction, and/or the phase gradient distribution in the y-direction. The processor 152 can also combine the two-dimensional images to generate a three-dimensional image of the object 30 or portions of the object 30.

In some embodiments, an output device (e.g., a printer, display, etc.) of the quantitative DIC device 100 can output various forms of data. For example, the quantitative DIC device 100 can output a two-dimensional local intensity image map, a two-dimensional phase gradient image map in and x-direction, a two-dimensional phase gradient image map in and y-direction, two-dimensional reconstructed image, a two-dimensional propagated image, and/or a three-dimensional image. The quantitative DIC device can also further analyze the two-dimensional wavefront data. For example, the quantitative DIC device 100 can use the intensity data to analyze biological properties of the object 30.

Modifications, additions, or omissions may be made to the method without departing from the scope of the disclosure. The method may include more, fewer, or other steps. Additionally, steps may be performed in any suitable order without departing from the scope of the disclosure.

Figure 16:
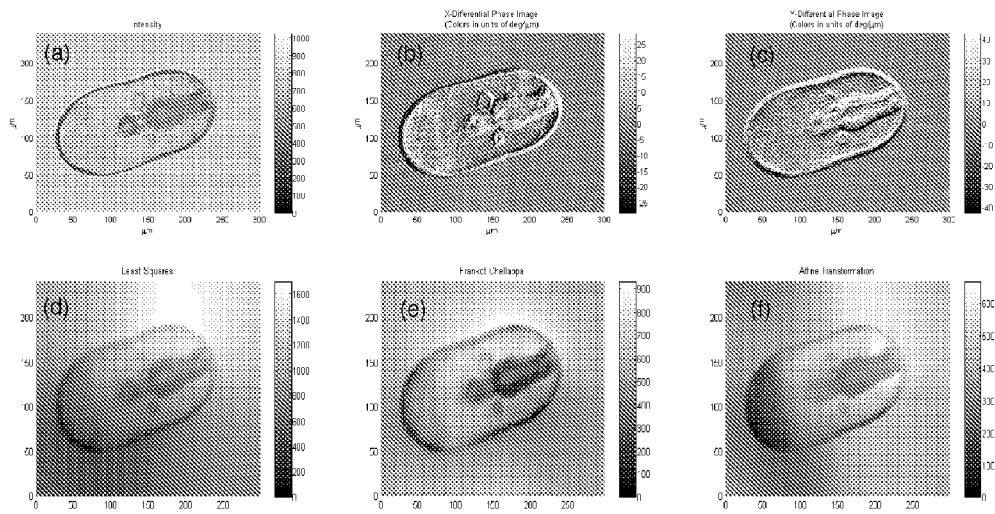
FIG. 16($a$) is an intensity/amplitude image taken of a starfish embryo using a quantitative DIC microscope having an SAI wavefront sensor, according to an embodiment of the invention.

The quantitative DIC device 100 of some embodiments can be used in various applications such as biological sample imaging. FIG. 16(a) is an intensity/amplitude image taken of a starfish embryo using a quantitative DIC microscope having an SAI wavefront sensor, according to an embodiment of the invention. FIG. 16(b) is an image based on phase gradient in the x direction taken of a starfish embryo using a quantitative DIC device having an SAI wavefront sensor, according to an embodiment of the invention. FIG. 16(c) is an image based on phase gradient in the y direction taken of a starfish embryo using a quantitative DIC device having an SAI wavefront sensor, according to an embodiment of the invention. FIGS. 16(d), 16(e) and 16(f) showcase some of the unwrapping algorithms when applied to the raw amplitude, differential phase x and differential phase y data of FIGS. 16(a), 16(b) and 16(c), according to embodiments of the invention. FIG. 16(d) is an image reconstructed using the least squares unwrapping method applied to the raw amplitude/intensity, phase gradient in the x-direction and phase gradient in the y-direction shown in FIGS. 16(a), 16(b) and 16(c) respectively. FIG. 16(e) is an image reconstructed using the Frankot Chellappa unwrapping method applied to the raw amplitude/intensity, phase gradient in the x-direction and phase gradient in the y-direction shown in FIGS. 16(a), 16(b) and 16(c) respectively. FIG. 16(f) is an image reconstructed using the Affine transformation unwrapping method applied to the raw amplitude/intensity, phase gradient in the x-direction and phase gradient in the y-direction shown in FIGS. 16(a), 16(b) and 16(c) respectively. With the wavefront computed (reconstructed), we can then perform computation-based sectioning via the approach outlined in the first section.

Figure 17:
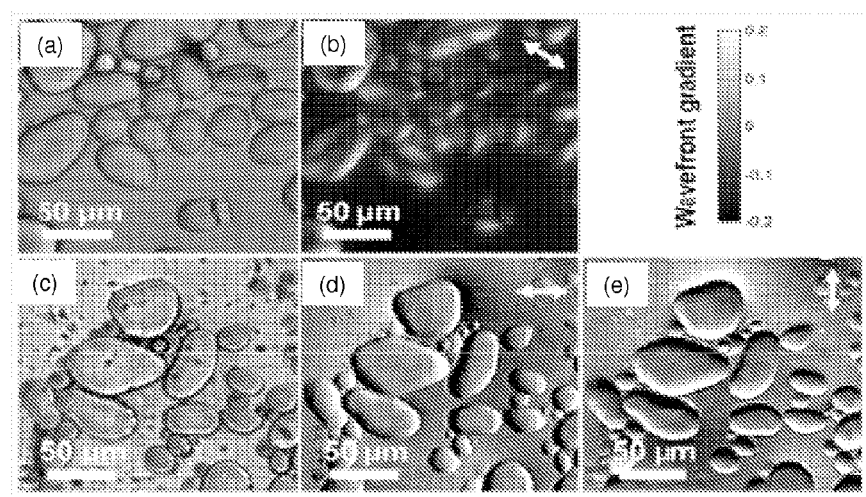
FIG. 17($a$) is an image of potato starch storage granules in immersion oil taken by a conventional transmission microscope.

FIG. 17(a) is an image of potato starch storage granules in immersion oil taken by a conventional transmission microscope. FIG. 17(b) is an image of potato starch storage granules in immersion oil taken by a conventional DIC microscope. FIG. 17(c) is an intensity image of potato starch storage granules in immersion oil taken by a quantitative DIC device in a microscope system, according to an embodiment of the invention. FIG. 17(d) is an artifact-free x-direction phase image of potato starch storage granules in immersion oil taken by a quantitative DIC device in a microscope system, according to an embodiment of the invention. FIG. 17(e) is an artifact-free y-direction phase image of potato starch storage granules in immersion oil taken by a quantitative DIC device 100 in a microscope system, according to an embodiment of the invention.

Birefringent objects such as the potato starch storage granules in FIGS. 17(a)-17(e) can alter polarization of the two displaced fields in a conventional DIC microscope, such that the subsequent combination of the two files in FIG. 2 is no longer describable by Eq. (1). This can give rise to the Maltese-cross-like pattern artifacts in the resulting conventional DIC images. FIG. 17(b) shows Maltese-cross-like pattern artifacts in the conventional DIC image of the potato starch storage granules.

In some embodiments, a quantitative DIC device 100 uses unpolarized light and does not rely on polarization for image processing. In these examples, the quantitative DIC device 100 can image birefringent samples (e.g., potato starch storage granules) without artifacts. FIGS. 17(d) and 17(e) show images of birefringent samples taken by a quantitative DIC device in a microscope system. In these figures, the birefringent images of the potato starch storage granules i.e. birefringent samples are without artifacts. Also, the dark absorption spots of the potato starch granules in the center of the intensity images in FIG. 17(c) do not appear in the phase images in FIGS. 17(d) and 17(e). This indicates that the quantitative DIC device 100 can separate the intensity variations of the image wavefront from the phase variations. This is advantageous over conventional DIC devices which cannot distinguish between the effects of absorption and phase variation and cannot provide quantitative phase measurements.

In one embodiment, the SAI wavefront sensor, a Shack-Hartmann wavefront sensor, or an OFM wavefront sensor can be placed into a camera system. One advantage to placing the wavefront sensor into a camera is that the camera can detect the phase gradient of the projected object wavefront in addition to the intensity information about the projected object wavefront.

In some embodiments, wavefront sensors 110/210 can be used with broadband illumination and/or monochromatic illumination. Wavefront sensors 110/210 apply to a monochromatic light field distribution in which k is well defined at each point on the image plane. However, wavefront sensing can also be used for a broadband light source and with situations where k at any given point may be a mix of different wave vectors. In this regard, wavefront sensors 110/210 can be used with broadband light illumination, monochromatic illumination with mixed k, and broadband light illumination with mixed k. An example of using broadband illumination by wavefront sensors 110/210 can be found in Cui, Xiquan, Lew, Matthew, Yang, Changhuei, Quantitative differential interference contrast microscopy based on structured-aperture interference," Applied Physics Letters Vol. 93 (9), 091113 (2008), which is hereby incorporated by reference in its entirety for all purposes.

In one embodiment, the diffraction spot size in a SAI wavefront sensor and the focal spot size in the Shack-Hartmann wavefront sensor of a quantitative DIC device 100 can be used to determine the spread of wave vector k at any given image point. The quantitative DIC device 100 in this embodiment can render images where the extent of scattering is plotted.

In one embodiment, the quantitative DIC device 100 can determine the proportionality of the phase gradient response of the wavefront sensor 110/210. The quantitative DIC device 100 measures the interference pattern as the wavefront sensor 110/210 is illuminated by a suitable illumination source (e.g., a collimated He—Ne laser beam) with a light having suitable properties (e.g., 632.8 nm wavelength, 25 mm beam diameter, and 4 mW power) and with a range of incident angles. The total transmission and the offsets of the zero-order spot in both x and y directions can be computed with a suitable method such as a least-square 2D Gaussian fit. The relationship between the offsets of the zero order spot and the normalized phase gradient can be approximately linear. The quantitative DIC device 100 estimates the constant that represents the approximately linear relationship between the offsets of the zero order spot and the normalized phase gradient.

V. Computer Devices

Figure 18:
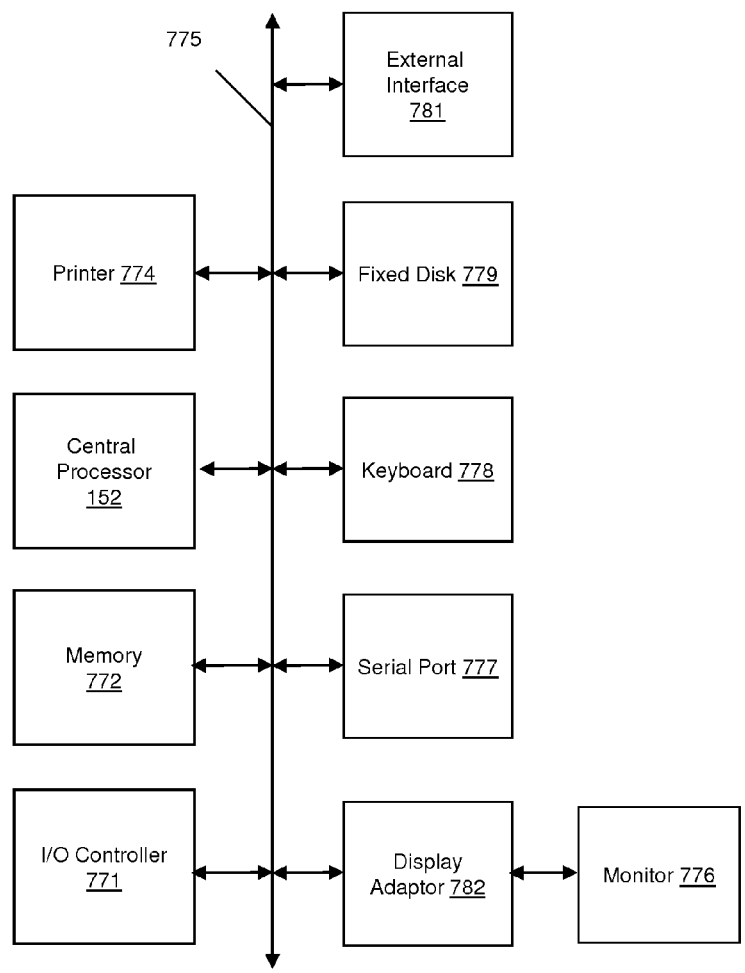
FIG. 18 shows a block diagram of subsystems that may be present in computer devices that are used in quantitative DIC device, according to embodiments of the invention.

FIG. 18 shows a block diagram of subsystems that may be present in computer devices that are used in quantitative DIC device 100, according to embodiments of the invention. For example, the host computer 150 or wavefront sensor 110/210 may use any suitable combination of components in FIG. 18.

The various components previously described in the Figures may operate using one or more computer devices to facilitate the functions described herein. Any of the elements in the Figures may use any suitable number of subsystems to facilitate the functions described herein. Examples of such subsystems or components are shown in a FIG. 18. The subsystems shown in FIG. 18 are interconnected via a system bus 775. Additional subsystems such as a printer 774, keyboard 778, fixed disk 779 (or other memory comprising computer readable media), monitor 776, which is coupled to display adapter 782, and others are shown. Peripherals and input/output (I/O) devices, which couple to I/O controller 771, can be connected to the computer system by any number of means known in the art, such as serial port 777. For example, serial port 777 or external interface 781 can be used to connect the computer apparatus to a wide area network such as the Internet, a mouse input device, or a scanner. The interconnection via system bus allows the central processor 152 to communicate with each subsystem and to control the execution of instructions from system memory 772 or the fixed disk 779, as well as the exchange of information between subsystems. The system memory 772 and/or the fixed disk 779 may embody a computer readable medium. Any of these elements may be present in the previously described features. A computer readable medium according to an embodiment of the invention may comprise code for performing any of the functions described above.

In some embodiments, an output device (e.g., the printer 774) of the quantitative DIC device 100 can output various forms of data. For example, the quantitative DIC device 100 can output a two-dimensional local intensity image map, a two-dimensional phase gradient image map in and x-direction, a two-dimensional phase gradient image map in and y-direction, two-dimensional reconstructed image, a two-dimensional propagated image, and/or a three-dimensional image. The quantitative DIC device 100 can also further analyze the two-dimensional wavefront data. For example, the quantitative DIC device 100 can use the intensity data to analyze biological properties of the object 30.

It should be understood that the present invention as described above can be implemented in the form of control logic using computer software in a modular or integrated manner. Based on the disclosure and teachings provided herein, a person of ordinary skill in the art will know and appreciate other ways and/or methods to implement the present invention using hardware and a combination of hardware and software.

Any of the software components or functions described in this application, may be implemented as software code to be executed by a processor using any suitable computer language such as, for example, Java, C++ or Perl using, for example, conventional or object-oriented techniques. The software code may be stored as a series of instructions, or commands on a computer readable medium, such as a random access memory (RAM), a read only memory (ROM), a magnetic medium such as a hard-drive or a floppy disk, or an optical medium such as a CD-ROM. Any such computer readable medium may reside on or within a single computational apparatus, and may be present on or within different computational apparatuses within a system or network.

A recitation of "a", "an" or "the" is intended to mean "one or more" unless specifically indicated to the contrary.

The above description is illustrative and is not restrictive. Many variations of the disclosure will become apparent to those skilled in the art upon review of the disclosure. The scope of the disclosure should, therefore, be determined not with reference to the above description, but instead should be determined with reference to the pending claims along with their full scope or equivalents.

One or more features from any embodiment may be combined with one or more features of any other embodiment without departing from the scope of the disclosure. Further, modifications, additions, or omissions may be made to any embodiment without departing from the scope of the disclosure. The components of any embodiment may be integrated or separated according to particular needs without departing from the scope of the disclosure.

All patents, patent applications, publications, and descriptions mentioned above are herein incorporated by reference in their entirety for all purposes. None is admitted to be prior art.

What is claimed is:

1. A method for computing depth sectioning of an object using a quantitative differential interference contrast device comprising a wavefront sensor with one or more structured apertures in a lensless aperture layer, a light detector, and a transparent layer between the lensless aperture layer and the light detector, the method comprising:
    detecting light received by the light detector through one of the one or more structured apertures, the light from an image wavefront induced by the object;
    measuring, by the wavefront sensor, an amplitude of the image wavefront based on the detected light;
    measuring, by the wavefront sensor, a phase gradient in two orthogonal directions of the image wavefront based on the detected light and based on depth of the transparent layer;
    reconstructing, by a processor, a reconstructed image wavefront using the measured amplitude and phase gradient based on the detected light through the one or more structured apertures in the lensless aperture array; and
    computing depth sectioning by propagating, by the processor, the reconstructed image wavefront to a first plane intersecting the object at a first depth through the object.

2. The method of claim 1, wherein computing depth sectioning also propagates the reconstructed image wavefront to a second plane intersecting the object at a second depth.

3. The method of claim 2, further comprising generating a three-dimensional image of a portion of the object based on the propagated image wavefronts at the first and second planes.

4. The method of claim 1,
    wherein computing depth sectioning also propagates the reconstructed image wavefront to a plurality of parallel planes intersecting the object, the planes substantially parallel to a surface of the light detector and at depths substantially extending through a dimension of the object; and further comprising generating a three-dimensional image of the object based on the propagated images wavefronts at two or more of the first plane and the plurality of parallel planes.

5. The method of claim 1, generating a two-dimensional image of the object at the first depth based on the propagated image wavefront at the first plane.

6. The method of claim 5, wherein the two-dimensional image is a cross-sectional image of the object.

7. The method of claim 1, wherein measuring an amplitude of the image wavefront based on the detected light comprises:
separating intensity data of the detected light associated with each structured aperture;
measuring a local amplitude associated with each structured aperture by summing the separated intensity data associated with each structured aperture; and
generating the amplitude of the image wavefront by compiling the local amplitudes measured at each structured aperture.

8. The method of claim 1, wherein measuring a phase gradient in two orthogonal directions of the image wavefront based on the detected light comprises:
separating intensity data of the detected light associated with each structured aperture;
measuring offsets in two orthogonal directions of the detected light at each structured aperture before and after the object is introduced; and
measuring a local phase gradient in two orthogonal directions at each structured aperture based on the offsets; and
generating the phase gradient in two orthogonal directions by compiling the local phase gradients measured at each structured aperture.

9. The method of claim 1, further comprising introducing the object which alters light from one or more illumination sources.

10. The method of claim 1, wherein receiving light by the light detector through the one or more structured apertures comprises:
generating, by the light detector, time varying data associated with the light received through the one or more structured apertures as the object moves through a fluid channel; and
compiling the time varying data to generate a two-dimensional light distribution.

11. A wavefront sensor comprising:
a lensless aperture layer having one or more structured apertures;
a light detector; and
a transparent layer between the lensless aperture layer and the light detector,
wherein the light detector measures the amplitude of a wavefront at a structured aperture of the one or more structured apertures, and the phase gradient in two orthogonal directions of the wavefront at the structured aperture based on light from the wavefront received through the structured aperture and based on depth of the trasparent layer.

12. The wavefront sensor of claim 11, wherein the light is unpolarized.

13. A quantitative differential interference contrast device comprising:
a wavefront sensor comprising
a lensless aperture layer having one or more structured apertures,
a light detector, and
a transparent layer between the lensless aperture layer and the light detector,
wherein the light detector measures the amplitude of a wavefront, and measures the phase gradient in two orthogonal directions of the wavefront based on light from the wavefront received through the one or more structured apertures and based on depth of the transparent layer; and
a processor communicatively coupled to the wavefront sensor, wherein the processor reconstructs a reconstructed image wavefront using the measured amplitude and phase gradient from the light detector.

14. The quantitative differential interference contrast device of claim 13, wherein the processor also propagates the reconstructed image wavefront to a first plane intersecting an object at a first depth through the object.

15. The quantitative differential interference contrast device of claim 13, further comprising a relay system for relaying the wavefront to the wavefront sensor.

16. The quantitative differential interference contrast device of claim 13, further comprising a raster scanning device for scanning the wavefront sensor.

17. The quantitative differential interference contrast device of claim 13, further comprising one or more illumination sources for providing light.

18. The method of claim 1, further comprising providing unpolarized light from an illumination source to the object to induce the image wavefront.

19. The method of claim 1, wherein the light detector of the wavefront sensor measures the amplitude in two orthogonal directions of the image wavefront.

20. The method of claim 1, wherein the phase gradient is measured by measuring offsets in two orthogonal directions of a zero order spot of the detected light and determining the phase gradient in two orthogonal directions based on the measured offsets.

21. The quantitative differential interference contrast device of claim 13, further comprising a light source providing unpolarized light to the object, which induces the image wavefront.

22. The wavefront sensor of claim 11, wherein the light detector measures the phase gradient by measuring offsets in two orthogonal directions of a zero order spot of the detected light and determining the phase gradient in two orthogonal directions based on the measured offsets.

23. The wavefront sensor of claim 11, wherein each of the one or more structured apertures comprise a non-circular light transmissive region extending in orthogonal directions.

24. The wavefront sensor of claim 23, wherein the non-circular light transmissive region is of a shape selected from the group consisting of a pedal shape or a ring shape.

25. The wavefront sensor of claim 11, wherein the one or more structured apertures comprises light transmissive regions in a plus sign configuration.

* * * * *